(12) United States Patent
Furner et al.

(10) Patent No.: US 9,352,064 B2
(45) Date of Patent: May 31, 2016

(54) WEARABLE CHEMICAL DISPENSER

(71) Applicant: S.C. Johnson & Son, Inc., Racine, WI (US)

(72) Inventors: Paul E. Furner, Racine, WI (US); Nitin Sharma, Kenosha, WI (US); Tai P. Luc, Oak Creek, WI (US); Zahra Tashakorinia, San Francisco, CA (US); Dirk K. Nickel, Mukwonago, WI (US); Terence Lup-ho Kwan, South San Francisco, CA (US); Evelyne Chaubert, San Francisco, CA (US); Jessica M. Gilbertson, San Francisco, CA (US); Wenson Chern, San Jose, CA (US); Evan A. Sparks, Madison, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 182 days.

(21) Appl. No.: 14/297,256

(22) Filed: Jun. 5, 2014

(65) Prior Publication Data

US 2015/0352241 A1    Dec. 10, 2015

(51) Int. Cl.
| | |
|---|---|
| *A61L 9/12* | (2006.01) |
| *A01M 7/00* | (2006.01) |
| *A01N 25/04* | (2006.01) |
| *A01M 29/12* | (2011.01) |
| *A01M 1/20* | (2006.01) |

(52) U.S. Cl.
CPC .............. *A61L 9/122* (2013.01); *A01M 1/2033* (2013.01); *A01M 7/0021* (2013.01); *A01M 29/12* (2013.01); *A01N 25/04* (2013.01); *A61L 9/12* (2013.01)

(58) Field of Classification Search
CPC ............... B01F 3/04; A61L 9/04; A61L 9/12; A61L 9/122
USPC ........... 96/417; 261/30, 100, 101; 239/53, 55, 239/56, 57, 58, 59
See application file for complete search history.

(56) References Cited

U.S. PATENT DOCUMENTS

| | | | |
|---|---|---|---|
| 2,585,339 | A | 2/1952 | Miller |
| 2,614,820 | A | 10/1952 | Boydjieff |
| 2,764,789 | A | 10/1956 | Zelenka |
| 3,633,881 | A | 1/1972 | Yurdin |
| 4,059,422 | A | 11/1977 | Steiner |

(Continued)

FOREIGN PATENT DOCUMENTS

| | | |
|---|---|---|
| EP | 1352562 A1 | 10/2003 |
| JP | 2014036677 A | 2/2014 |

(Continued)

OTHER PUBLICATIONS

PCT/US2015/033457 International Search Report and Written Opinion dated Sep. 2, 2015.

*Primary Examiner* — Robert A Hopkins

(57) ABSTRACT

Wearable devices for dispensing insect repellents, fragrances, and/or other chemicals along the outside of the clothing of a human are disclosed. They are of the type that are clipped onto a belt or the like, and use a powered fan to dispense active. They are configured with a first timer to account for a passive release rate of the active and a second timer to account for an active release rate of the active. The first time and second timer are in communication with a useful life indicator to provide a signal to a user of the device to indicate when the substrate in the device for containing the active should be replaced.

19 Claims, 27 Drawing Sheets

(56) References Cited

U.S. PATENT DOCUMENTS

| | | |
|---|---|---|
| 4,111,655 A | 9/1978 | Quincey |
| 4,166,087 A | 8/1979 | Cline et al. |
| 4,268,285 A | 5/1981 | Mason |
| 4,294,778 A | 10/1981 | DeLuca |
| 4,301,095 A | 11/1981 | Mettler et al. |
| 4,377,399 A | 3/1983 | Bryson |
| 4,396,557 A | 8/1983 | DeLuca |
| 4,830,791 A | 5/1989 | Muderlak et al. |
| 4,931,224 A | 6/1990 | Holzner, Sr. |
| 5,126,078 A | 6/1992 | Steiner et al. |
| 5,147,582 A | 9/1992 | Holzner, Sr. et al. |
| 5,193,984 A | 3/1993 | Lin |
| 5,223,182 A | 6/1993 | Steiner et al. |
| 5,234,162 A | 8/1993 | Sullivan |
| 5,305,541 A | 4/1994 | Simpson |
| 5,342,584 A | 8/1994 | Fritz et al. |
| 5,358,443 A | 10/1994 | Mitchell et al. |
| 5,370,829 A | 12/1994 | Kunze |
| 5,431,885 A | 7/1995 | Zlotnik et al. |
| 5,435,817 A | 7/1995 | Davis et al. |
| 5,498,397 A | 3/1996 | Horng |
| 5,547,616 A | 8/1996 | Dancs et al. |
| 5,562,407 A | 10/1996 | Cielo |
| 5,616,172 A | 4/1997 | Tuckerman et al. |
| 5,620,306 A | 4/1997 | Day |
| 5,641,343 A | 6/1997 | Frey |
| 5,695,692 A | 12/1997 | Kennedy |
| 5,704,832 A | 1/1998 | Borrell |
| 5,735,918 A | 4/1998 | Barradas |
| 5,753,000 A | 5/1998 | Chiu et al. |
| 5,829,188 A | 11/1998 | Tanitomi |
| 5,837,020 A | 11/1998 | Cartellone |
| 5,840,092 A | 11/1998 | Rick et al. |
| 5,925,172 A | 7/1999 | Rick et al. |
| 5,932,147 A | 8/1999 | Chen |
| 6,042,333 A | 3/2000 | Day |
| 6,050,016 A | 4/2000 | Cox |
| 6,050,551 A | 4/2000 | Anderson |
| 6,061,950 A | 5/2000 | Carey et al. |
| 6,102,660 A | 8/2000 | Lee |
| 6,103,201 A | 8/2000 | Green |
| 6,106,786 A | 8/2000 | Akahoshi |
| 6,154,607 A | 11/2000 | Flashinski et al. |
| 6,156,085 A | 12/2000 | Chiu et al. |
| 6,156,088 A | 12/2000 | Cardarelli |
| 6,192,621 B1 | 2/2001 | Fain |
| 6,241,218 B1 | 6/2001 | Tanitomi |
| 6,254,065 B1 | 7/2001 | Ehrensperger et al. |
| 6,293,044 B1 | 9/2001 | Feng |
| 6,315,821 B1 | 11/2001 | Pillion et al. |
| 6,328,791 B1 | 12/2001 | Pillion et al. |
| 6,361,752 B1 | 3/2002 | Demarest et al. |
| 6,371,450 B1 | 4/2002 | Davis et al. |
| 6,391,329 B1 | 5/2002 | Ito et al. |
| 6,392,549 B1 | 5/2002 | Wu |
| 6,435,828 B1 | 8/2002 | Bostwick |
| 6,447,587 B1 | 9/2002 | Pillion et al. |
| 6,482,365 B1 | 11/2002 | Soller |
| 6,497,753 B1 | 12/2002 | Gutmann |
| 6,508,868 B2 | 1/2003 | Pillion et al. |
| 6,511,531 B1 | 1/2003 | Cartellone |
| 6,514,052 B2 | 2/2003 | Bostwick |
| 6,553,711 B1 | 4/2003 | Feng |
| 6,569,387 B1 | 5/2003 | Furner et al. |
| 6,592,104 B2 | 7/2003 | Cox |
| 6,610,254 B1 | 8/2003 | Furner et al. |
| 6,623,265 B1 | 9/2003 | Day |
| 6,631,888 B1 | 10/2003 | Prueter |
| 6,632,405 B2 | 10/2003 | Lua |
| 6,719,217 B1 | 4/2004 | Tawara et al. |
| 6,769,631 B2 | 8/2004 | Brown |
| 6,783,081 B2 | 8/2004 | Pedrotti et al. |
| 6,783,117 B2 | 8/2004 | Wohrle |
| 6,857,214 B1 | 2/2005 | Pelissier |
| 6,881,382 B2 | 4/2005 | Goldstein et al. |
| 6,899,931 B2 | 5/2005 | Porchia et al. |
| 6,909,840 B2 | 6/2005 | Harwig et al. |
| 6,913,733 B2 | 7/2005 | Hardy et al. |
| 6,926,902 B2 | 8/2005 | Inoue et al. |
| 6,950,607 B2 | 9/2005 | Yip et al. |
| 6,966,665 B2 | 11/2005 | Limburg et al. |
| 7,007,861 B2 | 3/2006 | Ketcha et al. |
| 7,008,180 B2 | 3/2006 | Fujimori et al. |
| 7,040,548 B2 | 5/2006 | Rodgers |
| 7,112,232 B2 | 9/2006 | Chang et al. |
| 7,132,084 B1 | 11/2006 | Roumpos |
| 7,138,130 B2 | 11/2006 | Davis et al. |
| 7,152,809 B2 | 12/2006 | Ketcha et al. |
| 7,167,641 B2 | 1/2007 | Tam et al. |
| 7,168,630 B1 | 1/2007 | Ketcha et al. |
| 7,175,815 B2 | 2/2007 | Yamasaki et al. |
| 7,188,783 B2 | 3/2007 | Ivey et al. |
| 7,204,870 B2 | 4/2007 | Zobele et al. |
| 7,285,248 B2 | 10/2007 | Yamamoto et al. |
| 7,316,729 B2 | 1/2008 | Paterson et al. |
| 7,341,698 B2 | 3/2008 | Pedrotti et al. |
| 7,344,123 B2 | 3/2008 | Pankhurst et al. |
| 7,431,901 B2 | 10/2008 | Stiros et al. |
| 7,459,168 B2 | 12/2008 | Inoue et al. |
| 7,476,002 B2 | 1/2009 | Wolf et al. |
| 7,481,571 B2 | 1/2009 | Bistritzky et al. |
| 7,484,716 B2 | 2/2009 | Ford Morie et al. |
| 7,484,860 B2 | 2/2009 | Demarest et al. |
| 7,503,675 B2 | 3/2009 | Demarest et al. |
| 7,585,344 B2 | 9/2009 | Paterson et al. |
| 7,597,308 B1 | 10/2009 | Stucki |
| 7,597,857 B2 | 10/2009 | Reece |
| 7,621,511 B2 | 11/2009 | Hayes-Pankhurst et al. |
| 7,641,364 B2 | 1/2010 | Abbondanzio et al. |
| 7,670,035 B2 | 3/2010 | Tsai |
| 7,748,687 B2 | 7/2010 | Pankhurst et al. |
| 7,811,348 B2 | 10/2010 | Paterson et al. |
| 7,833,492 B2 | 11/2010 | Schumacher et al. |
| 7,887,759 B2 | 2/2011 | Triplett |
| 7,887,760 B2 | 2/2011 | Yamamoto et al. |
| 7,892,487 B2 | 2/2011 | Adair et al. |
| 7,917,018 B2 | 3/2011 | Schumacher et al. |
| 7,959,132 B2 | 6/2011 | Butler et al. |
| 8,025,845 B2 | 9/2011 | Yamasaki et al. |
| 8,048,379 B2 | 11/2011 | Sassoon |
| 8,074,970 B2 | 12/2011 | Pankhurst et al. |
| 8,137,629 B2 | 3/2012 | Faber et al. |
| 8,197,761 B1 | 6/2012 | Miller-Larry |
| 8,282,883 B2 | 10/2012 | Yamasaki et al. |
| 8,303,385 B2 | 11/2012 | Park |
| 8,328,894 B2 | 12/2012 | Thurin et al. |
| 8,347,549 B2 | 1/2013 | Durand et al. |
| 8,359,785 B2 | 1/2013 | Ohtsuka et al. |
| 8,367,011 B2 | 2/2013 | Yamamoto |
| 8,371,740 B2 | 2/2013 | Pestl et al. |
| 8,385,730 B2 | 2/2013 | Bushman et al. |
| 8,435,450 B2 | 5/2013 | Kawamura et al. |
| 8,449,828 B2 | 5/2013 | Yamamoto et al. |
| 8,524,158 B2 | 9/2013 | Shi et al. |
| 2002/0197189 A1 | 12/2002 | Lua |
| 2003/0012680 A1 | 1/2003 | Balsys |
| 2004/0146435 A1 | 7/2004 | Goldstein et al. |
| 2005/0019165 A1 | 1/2005 | Fujimori et al. |
| 2005/0191217 A1 | 9/2005 | Selander |
| 2005/0214175 A1 | 9/2005 | Barker |
| 2005/0220664 A1 | 10/2005 | Hitzler et al. |
| 2005/0226788 A1 | 10/2005 | Hrybyk et al. |
| 2005/0255008 A1 | 11/2005 | Lin |
| 2006/0039835 A1 | 2/2006 | Nottingham et al. |
| 2006/0043619 A1 | 3/2006 | Brown et al. |
| 2006/0137241 A1 | 6/2006 | Yamasaki et al. |
| 2007/0001024 A1 | 1/2007 | Wold et al. |
| 2007/0036673 A1 | 2/2007 | Selander |
| 2007/0087679 A1 | 4/2007 | Yamasaki et al. |
| 2007/0111654 A1 | 5/2007 | Yamasaki et al. |
| 2007/0158456 A1 | 7/2007 | Spector |
| 2007/0180801 A1 | 8/2007 | Paterson et al. |
| 2007/0180996 A1 | 8/2007 | Paterson et al. |
| 2008/0130266 A1 | 6/2008 | DeWitt et al. |

(56) References Cited

U.S. PATENT DOCUMENTS

| | | |
|---|---|---|
| 2008/0244954 A1 | 10/2008 | Shannon |
| 2008/0271338 A1 | 11/2008 | Muir et al. |
| 2008/0299014 A1 | 12/2008 | Kim |
| 2009/0008411 A1 | 1/2009 | Schumacher et al. |
| 2009/0060799 A1 | 3/2009 | Torres |
| 2009/0072783 A1 | 3/2009 | Gaspar et al. |
| 2009/0183636 A1 | 7/2009 | Levine et al. |
| 2009/0200393 A1 | 8/2009 | Avelar |
| 2010/0025490 A1 | 2/2010 | Bushman et al. |
| 2010/0044468 A1 | 2/2010 | Granger et al. |
| 2010/0064895 A1 | 3/2010 | Thurin et al. |
| 2010/0090022 A1 | 4/2010 | Hayashida |
| 2010/0129268 A1 | 5/2010 | Andersen |
| 2010/0132246 A1 | 6/2010 | Ohtsuka et al. |
| 2010/0150774 A1 | 6/2010 | Marchetti et al. |
| 2010/0177597 A1 | 7/2010 | Tsai |
| 2010/0180830 A1 | 7/2010 | Fritter et al. |
| 2010/0269826 A1 | 10/2010 | Colombo et al. |
| 2010/0284783 A1 | 11/2010 | Lolmede |
| 2010/0288847 A1 | 11/2010 | Gruenbacher et al. |
| 2011/0027124 A1 | 2/2011 | Albee et al. |
| 2011/0038761 A1 | 2/2011 | Saleh et al. |
| 2011/0049259 A1 | 3/2011 | Beland et al. |
| 2011/0108633 A1 | 5/2011 | Yamamoto et al. |
| 2011/0108634 A1 | 5/2011 | Yamamoto et al. |
| 2011/0110827 A1 | 5/2011 | Yamamoto et al. |
| 2011/0116977 A1 | 5/2011 | Yamamoto et al. |
| 2011/0134628 A1 | 6/2011 | Pestl et al. |
| 2011/0221079 A1 | 9/2011 | Yamasaki et al. |
| 2011/0268605 A1 | 11/2011 | Haran |
| 2012/0180666 A1 | 7/2012 | Lim et al. |
| 2012/0181350 A1 | 7/2012 | Snider |
| 2012/0183280 A1 | 7/2012 | Kowalec et al. |
| 2012/0205460 A1 | 8/2012 | Franks |
| 2012/0248136 A1 | 10/2012 | Meyers |
| 2012/0261484 A2 | 10/2012 | Blaylock et al. |
| 2012/0273978 A1 | 11/2012 | Sharma |
| 2012/0275932 A1 | 11/2012 | Sharma |
| 2012/0288414 A1 | 11/2012 | Shi et al. |
| 2013/0049236 A1 | 2/2013 | Garon et al. |
| 2014/0091487 A1 | 4/2014 | Belongia |

FOREIGN PATENT DOCUMENTS

| | | |
|---|---|---|
| WO | 9846280 A2 | 10/1998 |
| WO | 9902032 A1 | 1/1999 |
| WO | 0165931 A1 | 9/2001 |
| WO | 02060246 A1 | 8/2002 |
| WO | 03103387 A2 | 12/2003 |
| WO | 2005063013 A1 | 7/2005 |
| WO | 2006052519 A2 | 5/2006 |
| WO | 2006084317 A1 | 8/2006 |
| WO | 2007017742 A1 | 2/2007 |
| WO | 2008112545 A1 | 9/2008 |
| WO | 2009065629 A1 | 5/2009 |
| WO | 2009092135 A1 | 7/2009 |
| WO | 2009111903 A1 | 9/2009 |
| WO | 2009147330 A1 | 12/2009 |
| WO | 2011019404 A2 | 2/2011 |
| WO | 2011106889 A1 | 9/2011 |
| WO | 2011126208 A2 | 10/2011 |
| WO | 2012131232 A1 | 10/2012 |
| WO | WO 2012/154492 A1 | 11/2012 |
| WO | 2013032920 A1 | 3/2013 |

WEARABLE CHEMICAL DISPENSER

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

The present invention relates to wearable devices that dispense chemicals such as insect repellents and/or fragrances.

Various techniques have been developed to provide humans with protection from insect bites. For insect control inside buildings a primary emphasis is placed on trying to keep insects from entering the building at all (e.g. placing screens over windows). This sometimes is supplemented with chemical treatment of room air and/or the use of traps. See, for example, U.S. Pat. Nos. 6,582,714, 7,175,815, 7,621,511, and U.S. Patent Application Publication Nos. 2005/0079113, 2006/0039835, and 2006/0137241.

When the individual is outdoors where the area cannot be effectively screened, and the individual is mostly staying in a particular area (e.g. at a picnic, or on a patio near a building), traps and area-repellents are the primary focus.

Alternatively, when the individual is moving away from a single area that they control, individuals often apply a personal insect repellent to clothing or directly to their skin. However, some consumers have expressed a reluctance to apply insect repellents directly to their skin or to delicate clothing.

As a result, portable electrical devices having a fan and an insecticide source have been developed. These devices may have a clip so that they can easily be mounted on a belt, a purse, or even a pocket, and thus be "worn" by the consumer as they move outside. The device may draw air through, or blow air past, a substrate impregnated with an insect repellent or other air treatment chemical, thereby dispensing the active into the air, preferably (in the case of a repellent) along the outside of a human's clothing. See, for example, U.S. Pat. Nos. 6,926,902, 7,007,861, 7,152,809, 7,168,630, 7,175,815, 7,285,248, and 7,887,760, and U.S. Patent Application Publication No. 2009/0060799.

However, some such devices may blow the active too far out away from the human body, causing too little of the active to reach locations of primary concern (e.g. near ankles). Other such devices do not provide a way of minimizing waste of the active, such as while blower operation is suspended between uses. Still other such devices are unduly costly, are too heavy, or have other deficiencies.

The deficiencies in the above noted devices have been addressed by the wearable chemical dispensers described in U.S. Pat. Nos. 7,892,487, 7,833,492, 7,917,018, and 8,524, 158, and U.S. Patent Application Publication No. 2011/0038761. However, it is still desirable to improve this type of product further, particularly with respect to: (i) providing the user with an indication that the substrate impregnated with the insect repellent or other air treatment chemical needs to be replaced, (ii) assuring that the refill substrate is correctly positioned in the device, (iii) providing uniform dispersion of the air treatment chemical at high energy efficiency, and (iv) providing the user with means for positioning the dispenser on a surface or hanging the dispenser.

Hence, a need still exists to improve wearable chemical dispensers in these areas.

SUMMARY OF THE INVENTION

In one embodiment, a wearable device for dispensing an air treatment chemical is provided. The device includes a circular housing comprising an inlet for permitting air to enter into an interior space of the housing, and a plurality of outlets spaced substantially 360 degrees around the housing, wherein the outlets permit air mixed with air treatment chemical to exit the interior space. The device includes a substrate dimensioned to be positioned in the housing via a slot in the housing. The substrate bears an air treatment chemical. A centrifugal fan is mounted within the housing. The fan is capable of moving air from the inlet adjacent the substrate so as to mix air treatment chemical into the moving air, and then deliver a mixture of air and air treatment chemical through the outlets to outside of the housing. In one version of the device, the inlet comprises a first section including a plurality of spaced apart apertures and a cover section including a plurality of spaced apart vent openings, and the cover section is movable from a first position in which the cover section covers the plurality of spaced apart apertures of the first section to a second position in which the plurality of spaced apart vent openings of the cover section are at least partially aligned with the plurality of spaced apart apertures of the first section.

In another version of the device, a power supply and a motor are mounted within the housing. The motor is powered by the power supply, and the fan is connected to the motor. The power supply includes a battery, and the motor has a current draw such that power of the device is 50 milliwatts or greater when the battery is fully charged.

In another version of the device, the vent openings of the cover section include at least a first size of openings of a first inside diameter and a second size of openings of a second inside diameter smaller than the first inside diameter, and at least a first group of the first size of openings is arranged further away from a center of the cover section than a second group of the second size of openings.

In another version of the device, the vent openings of the cover section include a plurality of sizes of openings, and a size of openings having the largest inside diameter is arranged about half way between a center of the cover section and an outer periphery of the cover section.

In another version of the device, a clip is rotatably connected to an outer wall of the housing, and the clip is structured to rotate 360 degrees with respect to the housing. The clip may include a slot.

In yet another embodiment, a refill adapted for use in a wearable device for dispensing an air treatment chemical is provided. The wearable device includes a housing comprising an inlet for permitting air to enter into an interior space of the housing, and an outlet permitting air mixed with air treatment chemical to exit the interior space. The refill includes a substrate dimensioned to be positioned in the housing via a slot in the housing. The substrate has a first end, a second end opposite the first end, a first side, and a second side opposite the first side, and the substrate bears an air treatment chemical. The second side of the substrate includes an alignment profile that cooperates with an alignment structure in the slot such that the first end of the substrate faces away from an opening of the slot and the second side of the substrate faces the inlet when the substrate is positioned for use in the housing.

In one version of the refill, the substrate includes an outer wall, and the alignment profile is partially defined by a notch in a section of the outer wall adjacent the first end of the substrate.

In one version of the refill, the alignment profile is partially defined by a tab that extends away from the second side of the substrate adjacent the second end of the substrate.

In one version of the refill, the alignment structure in the slot comprises a stop rib extending away from the inlet. The notch travels past the stop rib when the substrate is inserted in the opening of the slot with the first end of the substrate facing into the interior space of the housing and the second side of the substrate facing the inlet.

In still another embodiment, a wearable device for dispensing an air treatment chemical is provided. The device includes a housing comprising an inlet for permitting air to enter into an interior space of the housing, and an outlet for permitting air mixed with air treatment chemical to exit the interior space. A substrate is positioned within the housing, and the substrate bears an air treatment chemical. A power supply mounted within the housing, and a motor is mounted within the housing. The motor is powered by the power supply. A fan is mounted within the housing and is connected to the motor. The fan is capable of moving air from the inlet adjacent the substrate so as to mix air treatment chemical into the moving air, and then deliver a mixture of air and air treatment chemical through the outlet to outside of the housing. The device includes a switch for activating and deactivating the motor. A top section of the housing is rotatably coupled to a bottom section of the housing, and the top section of the housing is rotatable to contact the switch and activate the motor.

In one version of the device, the top section of the housing has a first position for positioning the substrate within the housing, and the top section of the housing has a second position for securing the substrate within the housing, and the top section of the housing has a third position for contacting the switch.

The device may further include a controller in electrical communication with the switch and an indicator of useful life for the substrate. The controller executes a stored program to activate the indicator based on a signal from the switch.

In one version of the device, the controller executes the stored program to: (i) adjust a value of a counting device when the switch is contacted, and (ii) activate the indicator when the value of the counting device equals a predetermined value.

The device may include an actuator positioned within the housing, wherein the substrate actuates the actuator when the substrate is positioned within the housing, and a controller in electrical communication with the switch, the actuator, and an indicator of useful life for the substrate. The controller executes the stored program to: (i) start adjusting a value of a counting device when the substrate actuates the actuator; (ii) adjust the value of the counting device when the motor is activated; and (iii) activate the indicator when the value of the counting device equals a predetermined value. The counting device may include a first timer and a second timer, and actuation of the actuator initiates the first timer, and activation of the motor initiates the second timer. The value of the counting device can be adjusted based on first timing signals from the first timer and second timing signals from the second timer.

In yet another embodiment, a wearable device for dispensing an air treatment chemical is provided. The device includes a housing with an inlet for permitting air to enter into an interior space of the housing, and an outlet for permitting air mixed with air treatment chemical to exit the interior space, a substrate positioned within the housing where the substrate bears an air treatment chemical, and a power supply mounted within the housing. The device further includes a motor mounted within the housing, where the motor is powered by the power supply, a fan mounted within the housing and connected to the motor, where the fan is capable of moving air from the inlet adjacent the substrate so as to mix air treatment chemical into the moving air, and then deliver a mixture of air and air treatment chemical through the outlet to outside of the housing, and an actuator positioned within the housing such that the substrate actuates the actuator when the substrate is positioned within the housing. The device also includes a controller electrically connected with the actuator, a switch for activating and deactivating the fan, and an indicator of useful life for the substrate, where the controller executes a stored program to activate the indicator based on a signal from the actuator and/or switch.

In one aspect, a top section of the housing is rotatably coupled to a bottom section of the housing such that the top section of the housing can be rotated to activate the fan. In another aspect, the switch comprises a second actuator and a protrusion on the top section of the housing, where the protrusion contacts the second actuator to activate the fan. In yet another aspect, the controller executes the stored program to achieve a number of objectives. First, the program starts adjusting a value of a counting device when the substrate actuates the actuator. Second, the program adjusts the value of the counting device when the fan is activated. Third, the program activates the indicator when the value of the counting device equals a predetermined value.

In still another aspect, the counting device includes a first timer and a second timer, where actuation of the actuator initiates the first timer and activation of the fan initiates the second timer. In one aspect, the value of the counting device is adjusted based on first timing signals from the first timer and second timing signals from the second timer. In another aspect, the value of the counting device is based on a passive release rate of the substrate. In yet another aspect, the value of the counting device is further based on an active release rate of the substrate.

In one aspect, the indicator is an audible indicator, a visual indicator and/or a physical indicator. In another aspect, the indicator is a visual indicator.

In yet another embodiment, a wearable device for dispensing an air treatment chemical is provided. The device includes a housing with an inlet for permitting air to enter into an interior space of the housing, and an outlet for permitting air mixed with air treatment chemical to exit the interior space, a substrate positioned within the housing, where the substrate bears an air treatment chemical, and a power supply mounted within the housing. The device further includes a motor mounted within the housing, where the motor is powered by the power supply, a fan mounted within the housing and connected to the motor, such that the fan is capable of moving air from the inlet adjacent the substrate so as to mix air treatment chemical into the moving air, and then deliver a mixture of air and air treatment chemical through the outlet to outside of the housing and a controller in electrical communication with a switch for activating and deactivating the fan. The device also includes an indicator of useful life for the substrate, where the controller executes a stored program to activate the indicator based on a signal from the switch. A top section of the housing is rotatably coupled to a bottom section of the housing such that the top section of the housing is rotated to activate the fan.

In one aspect, the top section of the housing has a first position for positioning the substrate within the housing, a second position for securing the substrate within the housing, and a third position for activating the fan. In another aspect an actuator is positioned within the housing, such that the substrate actuates the actuator when the substrate is positioned within the housing. In still another aspect, the switch comprises a second actuator and a protrusion on the top section of the housing, where the protrusion contacts the second actuator to activate the fan.

In yet another aspect, the controller executes the stored program to accomplish a number of objectives. First, the program starts adjusting a value of a counting device when the substrate actuates the actuator. Second, the program adjusts the value of the counting device when the fan is activated. Third, the program activates the indicator when the value of the counting device equals a predetermined value. In one aspect, the counting device includes a first timer and a second timer, where actuation of the actuator initiates the first timer while activation of the fan initiates the second timer. In another aspect, the value of the counting device is adjusted based on first timing signals from the first timer and second timing signals from the second timer. In still another aspect, the value of the counting device is based on a passive release rate of the substrate. In one aspect, the value of the counting device is further based on an active release rate of the substrate. In another aspect, the indicator is an audible indicator, a visual indicator and/or a physical indicator.

In still another embodiment, a method for dispensing an air treatment chemical is provided. The method includes the step of providing a device including a housing. The housing has a bottom housing section, a top housing section rotatably coupled to the bottom housing, an inlet for permitting air to enter into an interior space of the housing, and an outlet for permitting air mixed with air treatment chemical to exit the interior space. The device also includes a power supply mounted within the housing, a motor mounted within the housing, where the motor is powered by the power supply, and a fan mounted within the housing and connected to the motor, where the fan being capable of moving air from the inlet adjacent the substrate so as to mix air treatment chemical into the moving air, and then deliver a mixture of air and air treatment chemical through the outlet to outside of the housing. The method further includes the steps of positioning a substrate bearing an air treatment chemical within the housing with the top housing section in a first position, rotating the top housing section from the first position to a second position to secure the substrate within the housing, and rotating the top housing from the second position to a third position, to activate the fan.

It is an advantage of the invention to provide a wearable chemical dispenser having a rotating slide cover to allow a user of the device to easily load a refill unit, secure the refill unit and turn the fan on and off to operate the dispenser.

It is a further advantage of the invention to provide a set of actuators integrated into the dispenser. The actuators can be configured to indicate to a user when the useful life of a refill unit has expired. The actuators can sense when a new refill unit is loaded as well as when the fan is on. Based on active and passive release rate data associated with a chemical in a refill unit, an indication can be made to a user as to when to replace the refill unit. It is a further advantage of the present invention to include an indicator of useful life, such as a LED to help convey the indication to a user based on signals associated with the actuators.

These and other advantages of the present invention will become better understood upon consideration of the following detailed description, drawings, and claims.

BRIEF DESCRIPTION OF THE DRAWINGS

Like reference numerals will be used to refer to like parts from Figure to Figure in the following detailed description.

DETAILED DESCRIPTION OF THE INVENTION

Figure 1:
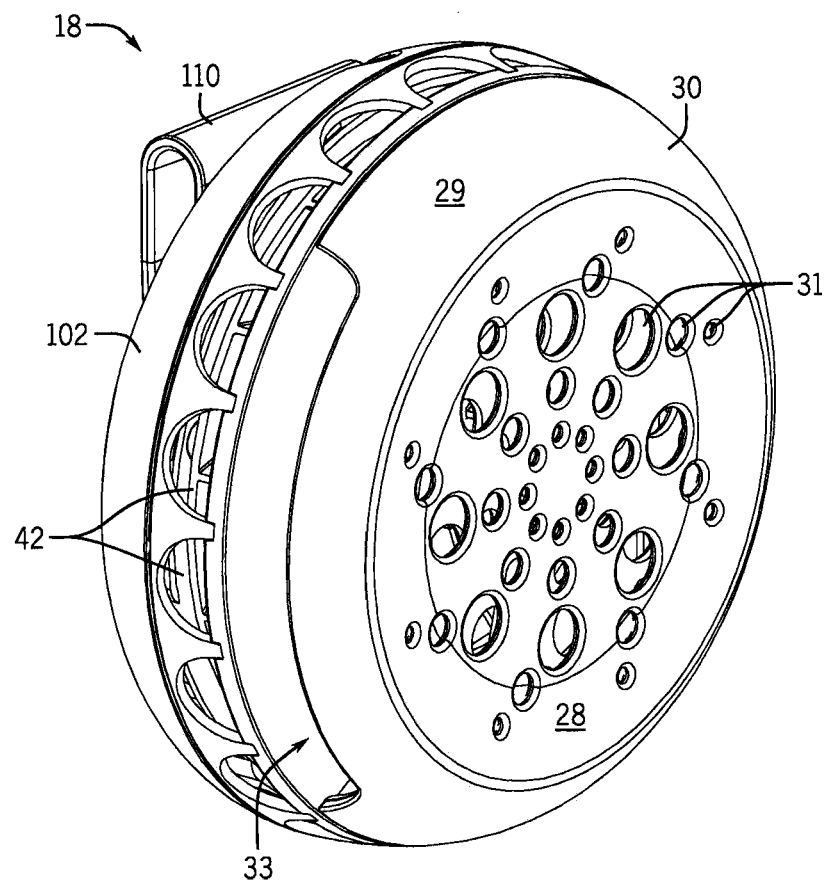
FIG. 1 is a left, top, front perspective view of a first embodiment of a wearable chemical dispenser according to the invention.
Figure 2:
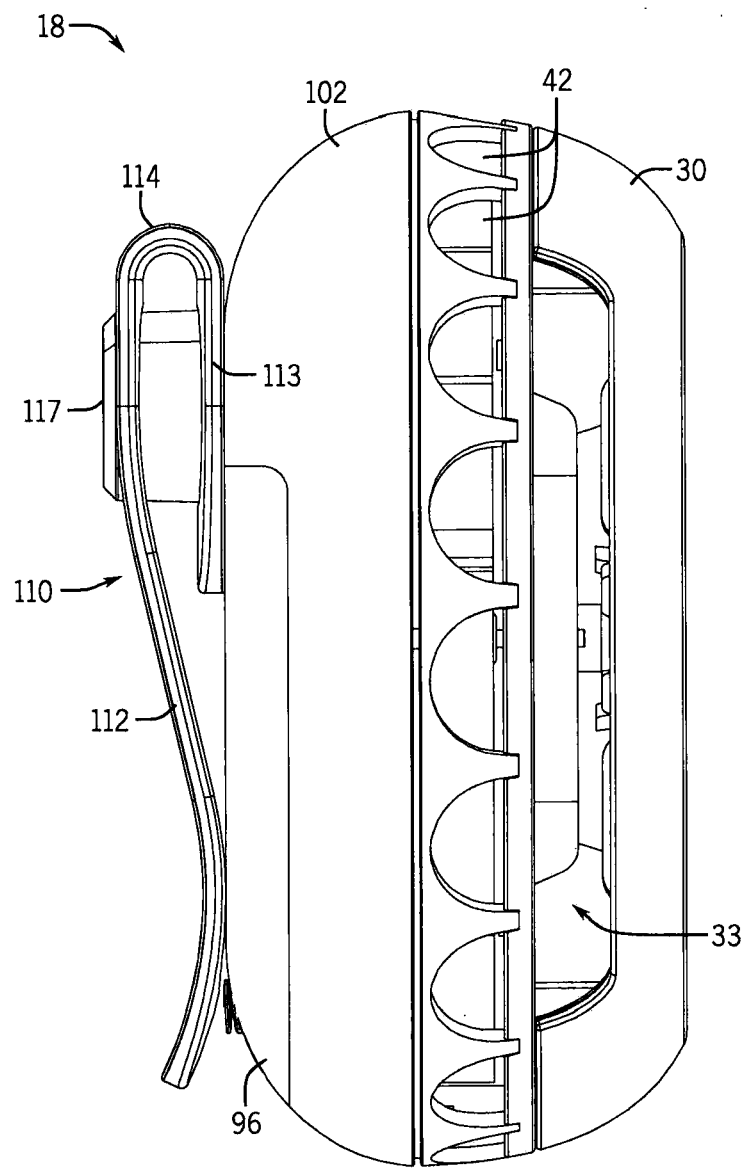
FIG. 2 is a left side elevation view of the dispenser of FIG. 1.

A non-limiting example of a wearable chemical dispenser 18 is shown in FIGS. 1-16. In one embodiment, the dispenser 18 is a portable, fan-based device for dispensing a chemical, such as an insect repellent, from a replaceable cartridge 44 (hereinafter, the 'refill unit') that is housed in the dispenser 18. Furthermore, the dispenser 18 can be attached with a clip 110 to a user's clothing (e.g., a belt) and is operated by rotating a slide cover 30 on the front face of the dispenser. The slide cover 30 can rotate between three settings including: (i) a 'load' setting for inserting/positioning the refill unit 44 in the dispenser 18, (ii) a 'lock' setting for securing the refill unit 44 in the dispenser 18, and (iii) an 'on' setting for operating the fan 60 to actively dispense the chemical in the refill unit 44.

One feature of the dispenser 18 is an indicator of useful life 49. It can be appreciated that the useful life of the refill unit 44 is, in part, determined by the passive and active rates at which chemical in the refill unit 44 is dispensed. In one aspect, the passive release rate can be defined as the rate at which the chemical is released from the refill unit 44 when the fan 60 is off and the dispenser 18 is not in operation (i.e., off). In another aspect, the active release rate can be defined as the rate at which the chemical is released from the refill unit 44 when the fan 60 is on and the dispenser 18 is in operation (i.e., on). In one example, the useful life indicator 49 is an LED that is lit to indicate to a user when the refill unit 44 should be replaced (e.g., the amount of chemical repellent remaining in the refill unit 44 is no longer effective for repelling insects). The useful life of the refill unit 44 is determined with two actuators housed in the dispenser 18. The first actuator is a refill switch actuator 36, which is triggered upon loading of a refill unit 44. The second actuator is an on/off switch actuator 56, which is triggered upon rotation of the slide cover 30 into the 'on' position. In one aspect, the refill switch actuator accounts for a passive release rate of chemical from the refill unit, while the on/off switch actuator accounts for an active release of rate of chemical from the refill unit.

FIGS. 1-5 and 10 show views of the assembled wearable chemical dispenser 18. The wearable chemical dispenser 18 includes a slide cover 30 disposed on a top housing section 20 (see FIGS. 8 and 9). Slide cover 30 and top housing 20 have side walls 29, 22 characterized by a generally spherical segment that extends from top walls 28, 23, respectively. In use, top wall 28 of slide cover 30 is typically frontally disposed and acts as a front cover in combination with top housing 20. A plurality of spaced apart apertures 24 are radially arranged in the top wall 23 of the top housing section 20. The apertures 24 provide an inlet for permitting air to enter into an interior space of the wearable chemical dispenser 18.

Slide cover 30 also possesses a plurality of spaced apart apertures 31 radially arranged in top wall 28. The apertures 31 provide an inlet for permitting air to enter into an interior space of the wearable chemical dispenser 18 when aligned with apertures 24 in top wall 23 of top housing 20. A further aspect of slide cover 30 is a cam projection 32 that extends through a semi-circular slot 27 in top housing 20 (see FIG. 9). Slide cover 30 is coupled to the top housing section 20 such that the slide cover 30 can rotate with respect to the top housing section 20. Slide cover 30 can be rotated between three distinct positions including a 'load' position, a 'lock' position and an 'on' position. In the 'lock' position, the slide cover 30 shields the apertures 24 that are radially arranged in the top wall 23 of the top housing section 20. In the 'on' position, the openings 31 of the slide cover 30 align with the apertures 24 that are radially arranged in the top wall 23 of the top housing section 20.

Figure 10:
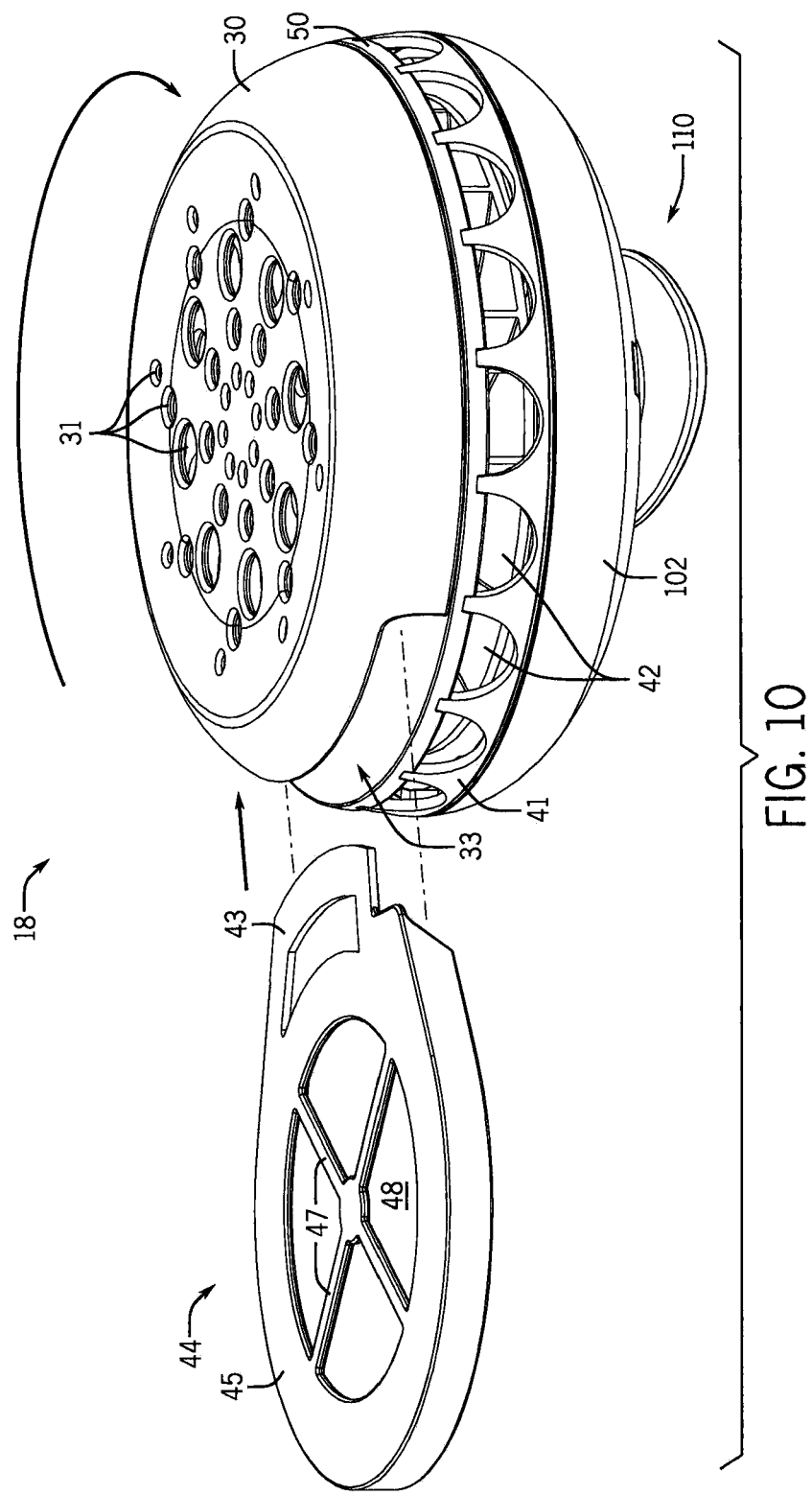
FIG. 10 is a left, bottom, front perspective view of the dispenser of FIG. 1 illustrating a method of loading a refill unit into the dispenser.

As illustrated in FIG. 10, a refill unit 44 is provided with the wearable chemical dispenser 18. When the top housing section 20 and the frame 50 are assembled (see, e.g., FIGS. 6-7), a housing having an interior space is formed. In the 'loading' position, the slide cover 30 and top housing 20 align to form a refill loading slot 33 through which the refill unit 44 can pass in order to be loaded into the interior space in wearable dispenser 18. When slide cover 30 is rotated in direction R to either the 'lock' position or the 'on' position, a portion of side wall 29 of slide cover 30 is positioned over (and therefore prevents access to) loading slot 33.

As shown in FIG. 10, the refill unit 44 has a generally slab-like support structure 45. In top plan view, the refill unit 44 has an essentially pear shaped overall appearance, with a generally circular portion at one end and a tabular portion at another end. There is a spoke support 47 across a circular opening through the refill unit 44. Across the spoke support 47 is positioned a fabric substrate 48. When air is drawn in, the air passes through the fabric substrate 48. The choice of the fabric, and its porosity, the speed of the air flow, and the vapor pressure of the active ingredient, are the main factors in coordinating the speed of use up of the active with counter for activating a useful life indicator 49 (see FIGS. 4-5 and 7-8) that can be viewed through a window 25 in the bottom cover 102. A non-limiting example refill unit has a twelve hour active use life (i.e., fan on). Indicator 49 is designed to provide an alert to a user of the wearable dispenser 18 upon the expiration of the useful life of the refill unit. Methods for determining when to activate indicator 49 are described in detail below.

By impregnating the fabric substrate 48 with an appropriate air treatment chemical, air entering the dispenser will pick up some of the volatile chemical, and dispense it out of the dispenser. Active release rates of 0.2 milligrams per hour (mg/hr) or higher are preferred. Particularly preferred active ingredients are metofluthrin, transfluthrin, prallethrin, vaporthrin, tefluthrin, and esbiothrin or other synthetic pyrethroids. The impregnation material can be pure active, or for ease of handling the material can be dissolved in a hydrocarbon or other solvent. Alternatively, or in addition, the fabric may also bear a fragrance, a deodorizer, or other air treatment chemical. It is preferred to have the fabric substrate 48 configured so that the pressure drop across the substrate is no more than 40 Pascal (Pa). Suitable fabrics can be made of woven or non-woven materials providing only minimal resistance to the airflow.

The fabric substrate 48 should also be capable of holding active ingredient dosed onto the material and also allow ready migration of the active to the surface so as to allow its evaporation in response to the airflow. Suitable materials include, only by way of example, polyester, polypropylene, cotton, cellulose, poly-rayon, and other similar fabrics. These can be non-wovens with basis weights ranging from 10 grams per square meter (g/m$^2$) to 40 grams per square meter (g/m$^2$), fabricated from synthetic, natural, or combined synthetic and natural polymeric materials.

The ideal fabric substrate 48 should also allow for wicking of the active ingredient following dosing so as to ensure efficient distribution throughout the substrate, and thereafter allow migration of active ingredient to the substrate surface to replenish the active ingredient that is being evaporated by the passing airflow. Dosing may be by dropping, spraying, printing, or other conventional delivery of a liquid active ingredient to the substrate. A particularly desirable fabric is a non-woven felted material with a basis weight of 20-30 g/m$^2$ fabricated from polyethylene terephthalate.

Figure 11:
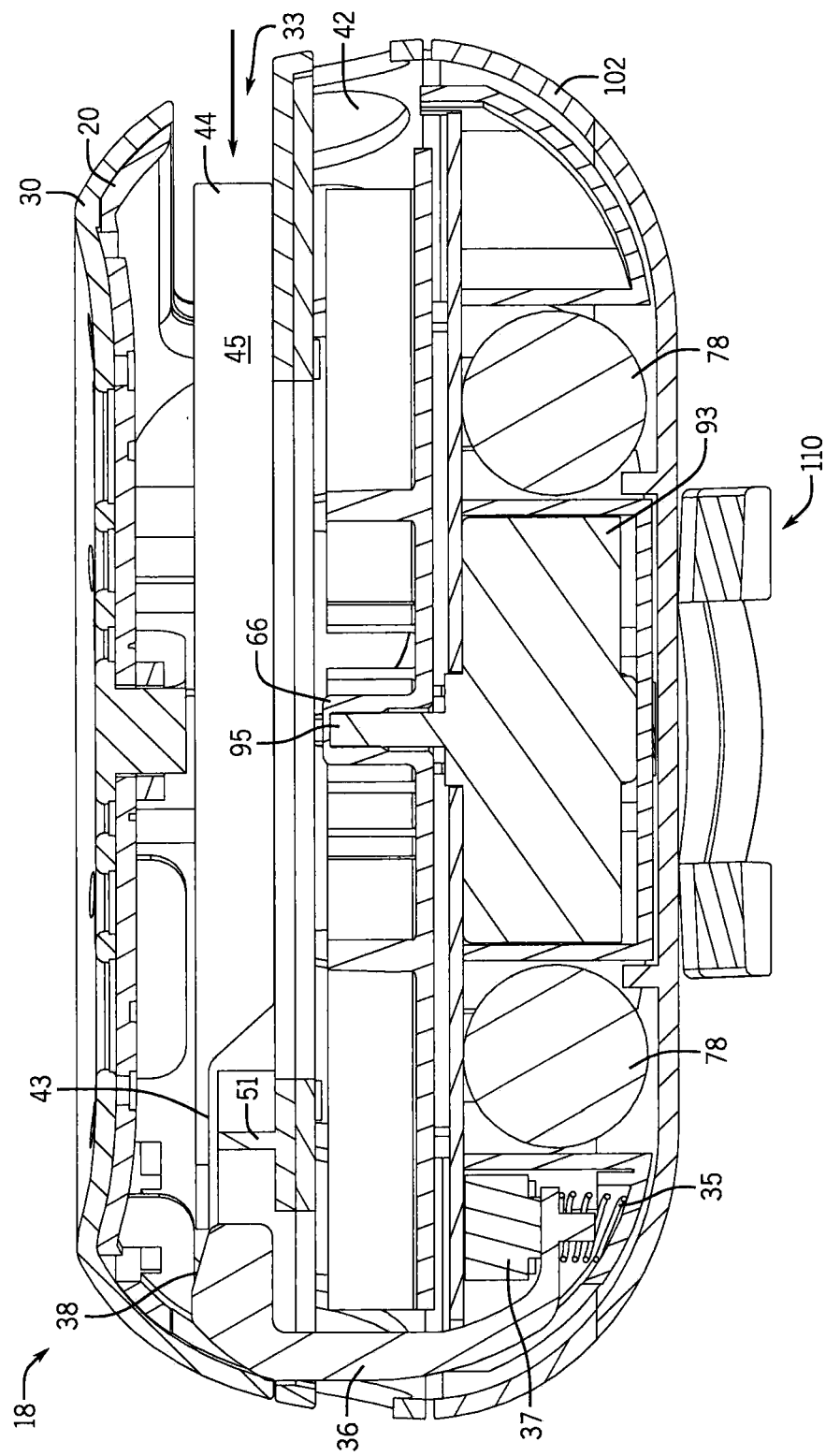
FIG. 11 is a cross-section view taken along line 6-6 of FIG. 4 illustrating the dispenser of FIG. 1 just prior to actuation of the refill switch actuator during loading of the refill unit.
Figure 12:
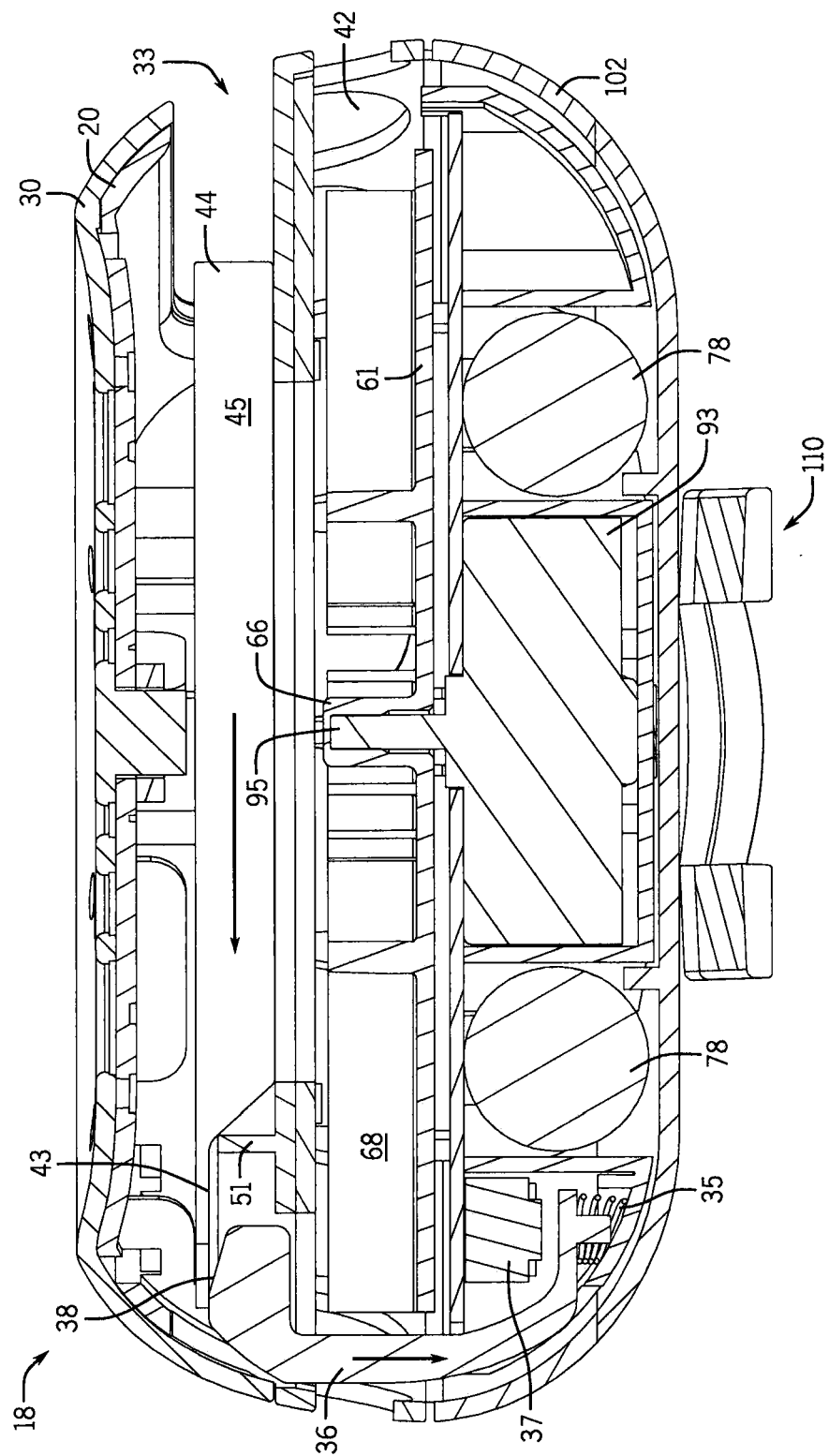
FIG. 12 is a cross-section view taken along line 6-6 of FIG. 4 illustrating the dispenser of FIG. 1 just after actuation of the refill switch actuator during loading of the refill unit.
Figure 13:
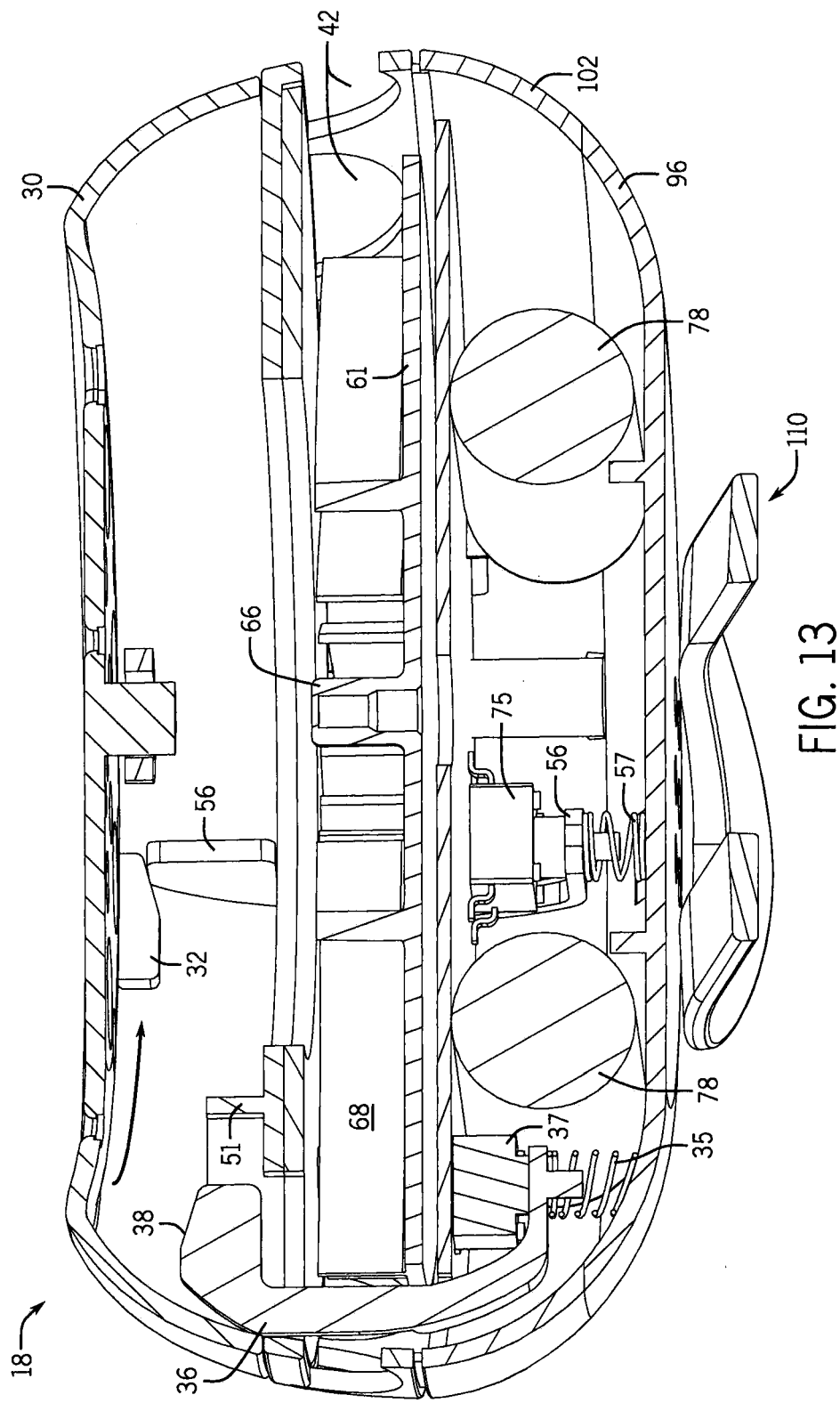
FIG. 13 is a cross-section view taken along line 13-13 of FIG. 4 illustrating the dispenser of FIG. 1 just prior to actuation of the on/off switch actuator during rotation of the of slide cover to the 'on' position.
Figure 14:
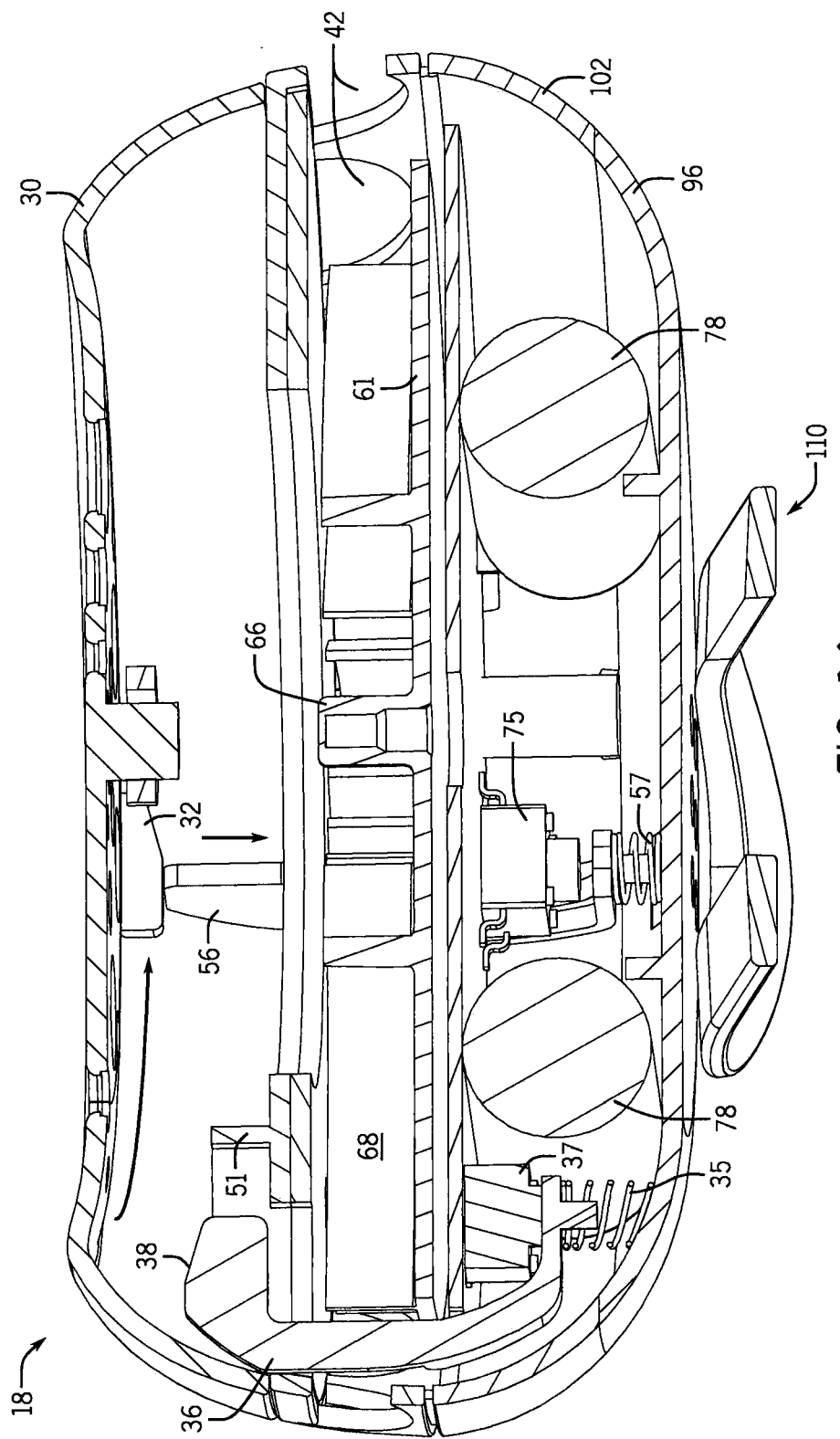
FIG. 14 is a cross-section view taken along line 13-13 of FIG. 4 illustrating the dispenser of FIG. 1 just after actuation of the on/off switch actuator during rotation of the of slide cover to the 'on' position.

A frame 50 is located below the refill unit 44 in the wearable chemical dispenser 18. The frame 50 has a generally circular perimeter, and supports the refill unit 44 (see FIG. 8). Note that the tabular portion 43 of the refill unit 44 is thinner than the circular portion of the refill unit 44. The tabular portion 43 is designed to pass over a raised feature 51 on the top side of frame 50, and to thereby prevent a consumer from loading the refill unit 44 incorrectly into the dispenser 18. Furthermore, the tabular portion 43 of the refill unit 44 is designed to actuate a refill switch actuator 37 positioned within the wearable dispenser 18. The interaction between the tabular portion 43 of the refill unit 44 with refill switch actuator 36 is illustrated in FIGS. 11-12. Refill switch actuator 36 is positioned such that a first end 39a contacts the tabular portion 43 of refill unit 44 when refill unit 44 is loaded by movement in direction D into the wearable dispenser 18. A second end 39b of the actuator 36 contacts a tactile switch 37 positioned in chassis 80. The refill switch actuator is biased towards the top face of the dispenser with a resistance means such as spring 35. The first end of the actuator 36 has a cam surface 38 such that the tabular portion 43 displaces actuator 36 when refill unit 44 is loaded into wearable dispenser 18. Displacement of actuator 36 is detected by tactile switch 37, which is in electrical communication with printed circuit board (PCB) 70.

Figure 8:
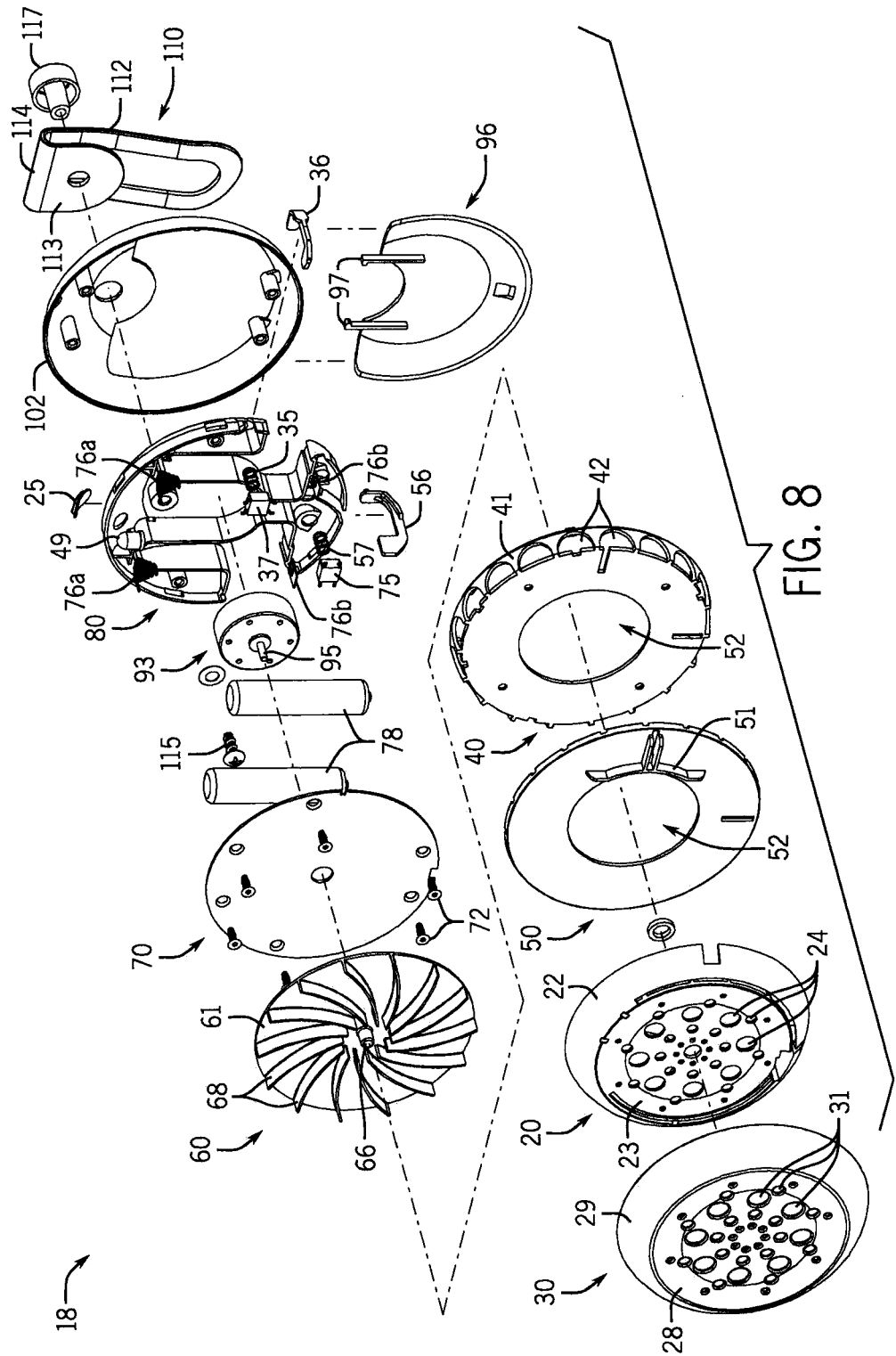
FIG. 8 is an exploded perspective view of the dispenser of FIG. 1.
Figure 9:
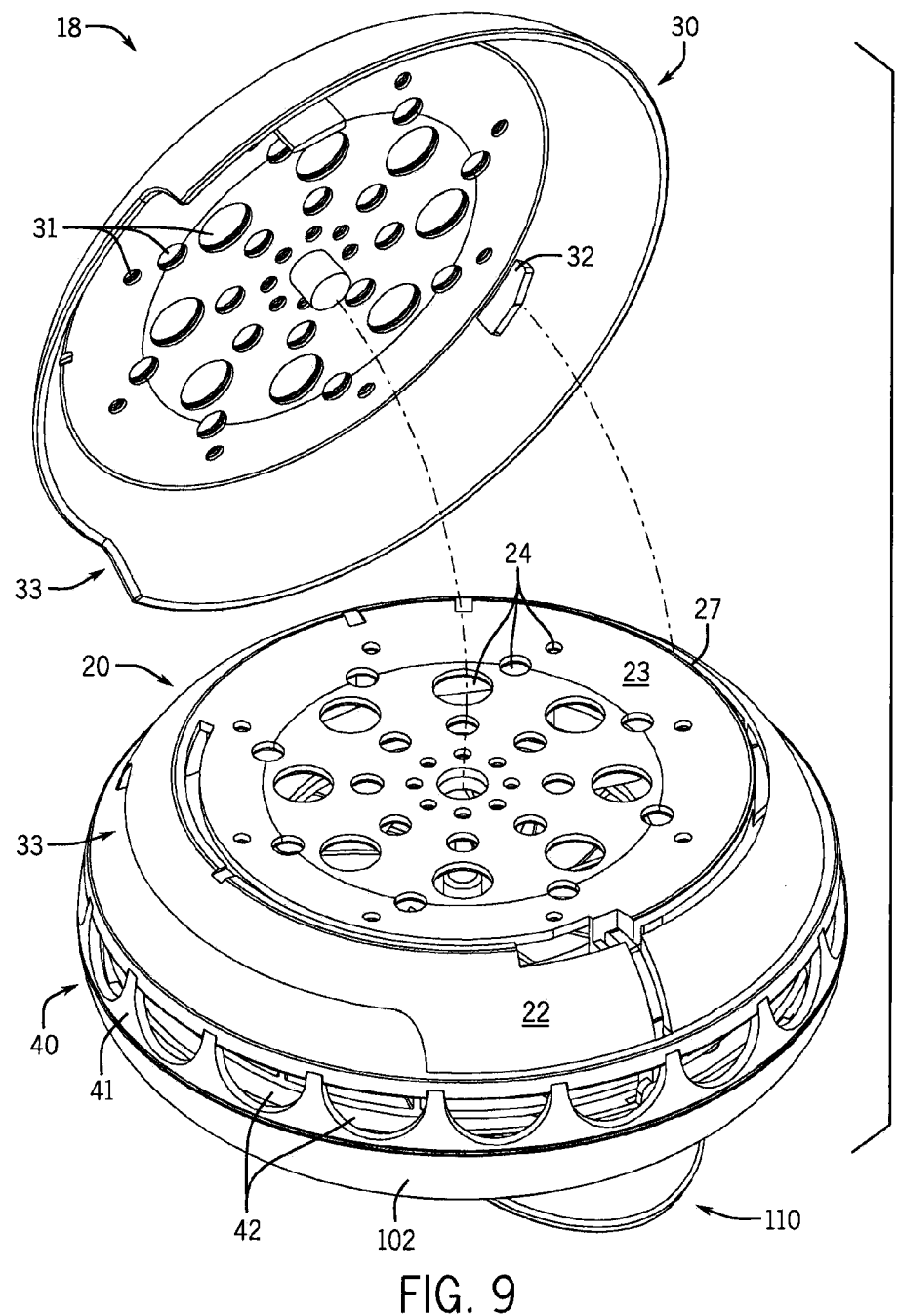
FIG. 9 is a left, bottom, front perspective view of the dispenser of FIG. 1 showing the alignment of the slide cover with the top housing.

Frame 50 is disposed on a fan housing 40. Both frame 50 and fan housing 40 are generally ring-shaped. The circular openings in frame 50 and fan housing 40 are aligned when the dispenser 18 is assembled. Referring to FIG. 8, the dispenser is assembled such that refill unit 44 is situated above frame 50, fan housing 40 and fan 60, in that order. This arrangement allows are to be drawn through refill unit 44 and circular opening 52. As described further on, this air, which is now mixed with chemical released from refill unit 44 can pass through openings 42 in sidewall 41 of fan housing 40.

Figure 15:
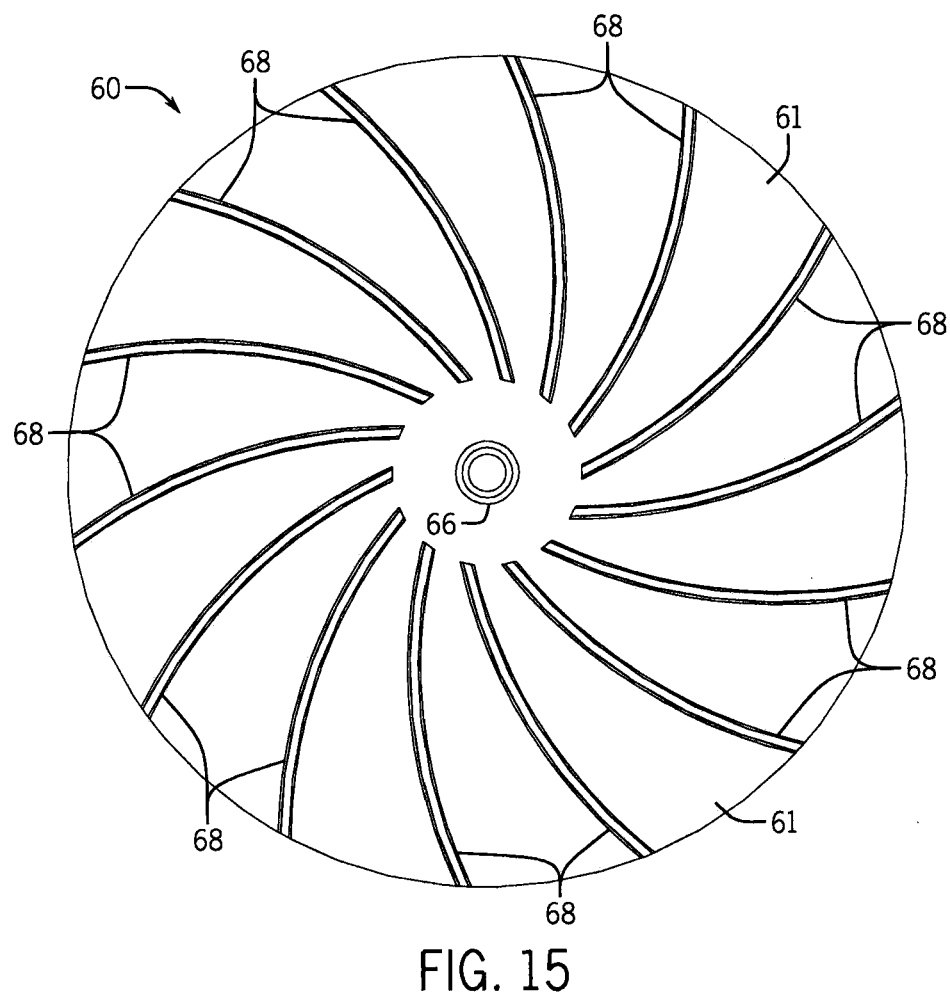
FIG. 15 is a top plan view of the rotor fan of the dispenser of FIG. 1.

Looking at FIGS. 8 and 15, there is shown a fan 60 of the wearable chemical dispenser 18. The fan 60 has a generally disk shaped rotor 61 that includes a tubular mounting element 66 on the axis of the rotor 61. The preferred fan 60 includes fourteen fan blades 68 (see FIG. 15). It has been discovered that a fan configuration, which results in an ideal balance of airflow and minimal power consumption for the wearable chemical dispenser 18, includes twelve to eighteen fan blades. Preferably, the fan produces an average volumetric flow rate of air of 1.4 to 3 cubic feet per minute (with the refill unit 44 installed) over the life (e.g., at least eight, and most preferably at least twelve hours) of a refill unit 44. Typically, the fan will operate at 3000-5000 rpm. In one example wearable chemical dispenser 18, over the life (e.g., twelve hours) of a refill unit 44, the consumed power from the power supply is 0.20 watts or less. In one example embodiment, over a twelve hour life of a refill unit 44, the consumed power from the power supply is about 0.19 watts while maintaining an average volumetric flow rate of air of at least 1.6 cubic feet per minute over the twelve hour period. When using a battery for the power supply, the voltage will vary during discharge. However, the power consumed can be determined from the total energy consumed divided by the total time.

The wearable chemical dispenser 18 includes an electrical power supply. In the example embodiment shown, a second tactile switch 75 of the power supply is in electrical communication with battery contacts 76a to complete an electrical circuit with batteries 78 and the battery contacts 76b to provide electricity to tactile switch 75. When a user rotates the slide cover 30 from the 'lock' position to the 'on' position, the cam projection 32 of the slide cover 30 is driven into the on/off switch actuator 56 which then contacts tactile switch 75 to turn on the power supply. Analogous to refill switch actuator 36, on/off switch actuator is biased towards the front face of the dispenser 18 with a resistance means such as spring 57.

The power supply is also in electrical communication with PCB 70 and tactile switch 37. As described previously, when a user inserts the refill unit 44 into the dispenser 18 while the slide cover 20 is in the 'load' position, the refill switch actuator 36 triggers tactile switch 37. In one example of wearable dispenser 18, activation of tactile switch 37 completes a circuit with batteries 78 to supply power to PCB 70 in order to activate a first counter (passive counter). Rotation of the top cover 30 from the 'lock' position to the 'on' position, in another aspect, turns on the fan motor 93 and also activates a second counter (active counter).

One method to accurately indicate to a user the end of the useful life of the refill unit 44 makes use of the passive and active counters. For example, if the passive counter is activated when the refill unit 44 is inserted into the dispenser 18, then the passive counter can be used to measure the elapsed time, $t_P$, since the initial loading of the refill unit 44. In one aspect, the elapsed time, $t_P$, is correlated with the passive release rate. If a particular refill unit 44 has a passive release rate that corresponds with a useful life of fourteen days, then the passive counter can be used to determine when $t_P$=fourteen days in order to alert a user via activation of the indicator of useful life 49.

In another example, if the active counter is triggered when the fan 60 is turned on (i.e., by rotating the slide cover 30 to the 'on' position), then the active counter can be used to measure the elapsed time, $t_A$, during which the dispenser 18 is in active use. In one aspect, the elapsed time, $t_A$, is correlated with the active release rate. If a particular refill unit 44 has an active release rate that corresponds to a useful life of twelve hours, then the active counter can be used to determine when $t_A$=twelve hours in order to alert a user via activation of the indicator of useful life 49.

In yet another example, $t_A$ and $t_P$ can be combined to more accurately determine the useful life of the refill unit 44. In this case involving two counters, the useful life is evaluated as a function of both $t_A$ and $t_P$. Expressed in the form of an equation, $f(t_A, t_P)=x$, where the indicator 49 is activated when x exceeds a threshold value $x_T$.

In still another example, a single counter is used to determine the useful life of the refill unit 44. Here, one approach is to configure the single counter to count from an initial value $x_0$ to a predetermined threshold value $x_T$. The rate at which the counter is incremented (or decremented) can be correlated with active and passive release rate data. In a one embodiment of a single counter approach, the counter is initialized when the refill unit 44 is loaded into the dispenser 18 and is incremented at a first rate corresponding to the passive release rate. When the fan 60 is turned on by rotating the slide cover 30 to the 'on' position, the counter is incremented at a second rate corresponding to the active release rate. If the fan 60 is turned off, by rotating the slide cover 30 to the 'lock' position, then the counter is again incremented based on the first rate.

With respect to the single counter approach, the rates at which the counter is incremented can be constant or variable. If it is determined that the active and/or passive release rates of a given chemical vary over time, it can be desirable to allow the rates at which the counter is incremented to vary as a function of time. For example, activation of the refill switch actuator 36 initializes the counter, records a time stamp, $t^o$, and increments the counter at a first (passive) rate that is a function of the elapsed time (i.e., $t-t^o$, the amount of time the refill unit 44 has been in the dispenser 18). Activation of the on/off switch actuator 56 increments the counter at a second (active) rate that is also a function of the elapsed time. Deactivation of the on/off switch actuator 56 causes the counter to once again increment at the first (passive) rate, which is still a function of the total elapsed time. In one aspect, rates are determined through the use of a look up table where the first and second rates are determined as a function of elapsed time. The look up table can be populated with data based on experimental results and/or correlations for measured active and passive release rates for a given chemical. However, it should be appreciated by the skilled artisan that there are many ways to implement a system for indicating to a user the end of a useful life of a refill unit 44 with the present wearable chemical dispenser 16.

Figure 16:
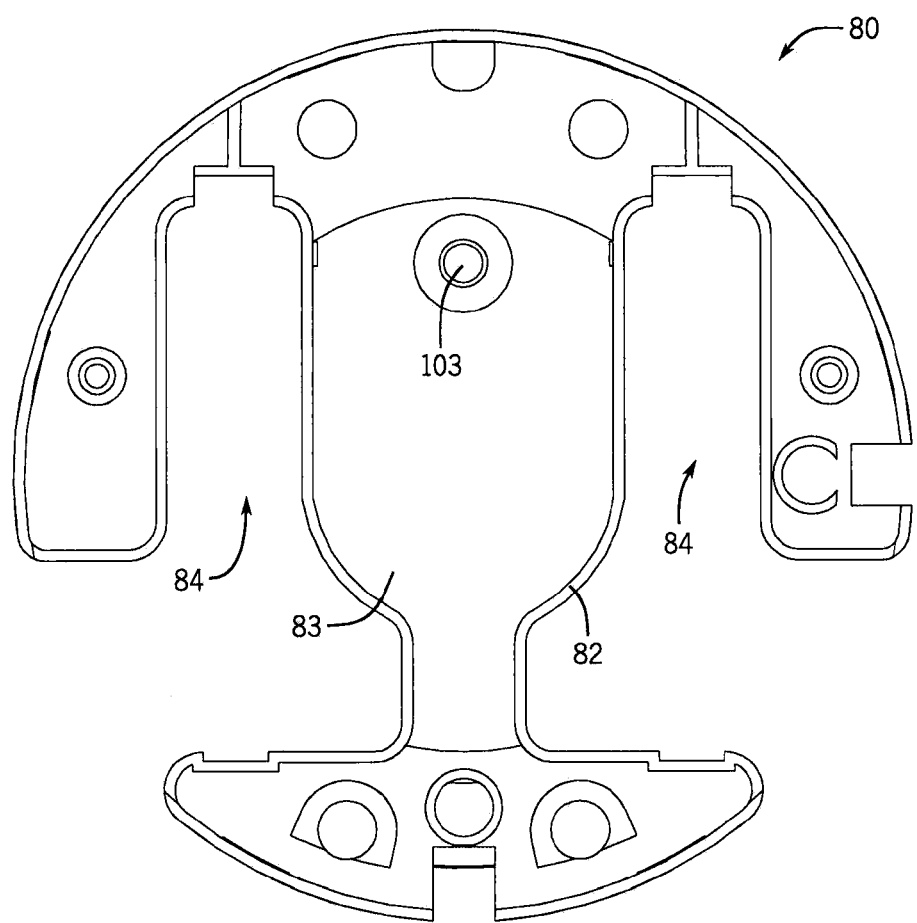
FIG. 16 is a top plan view of the chassis of the dispenser of FIG. 1.
Figure 17:
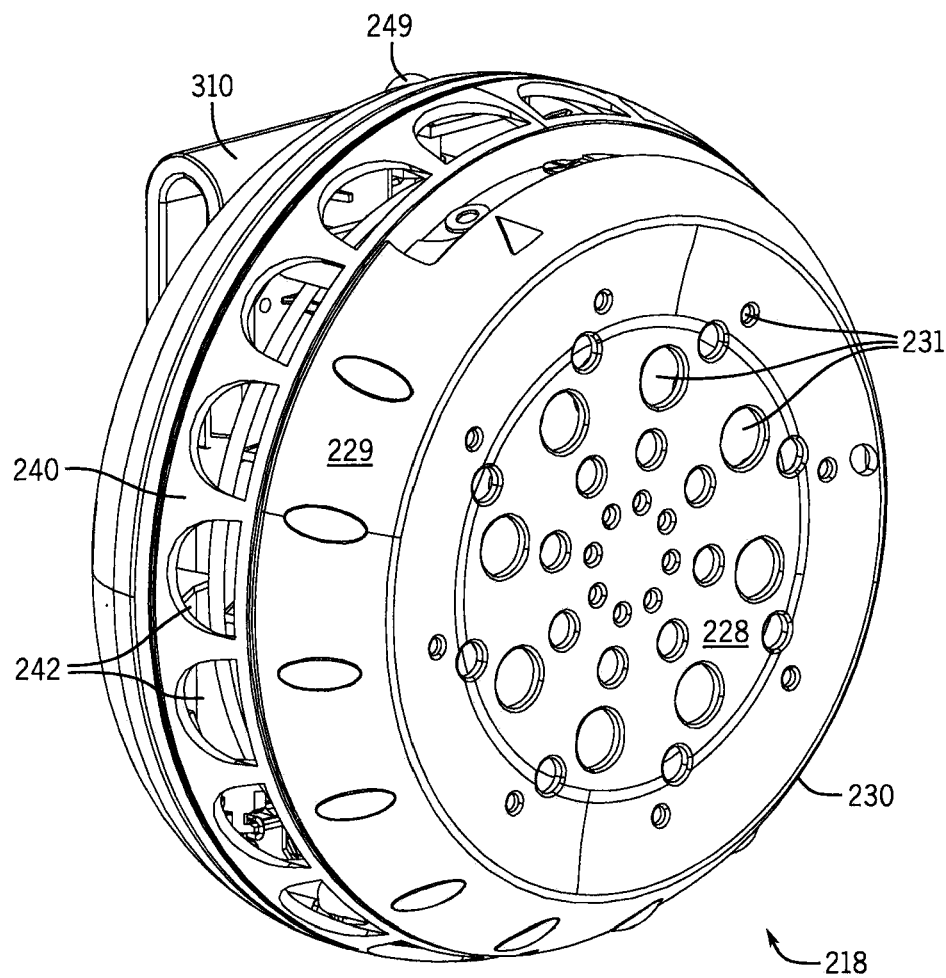
FIG. 17 is a left, top, front perspective view of a second embodiment of a wearable chemical dispenser according to the invention.

Looking at FIGS. 8 and 16, the wearable chemical dispenser 18 includes a chassis 80 for mounting various components of the wearable chemical dispenser 18 and for contributing to the control of air flow from the dispenser 18. When the PCB 70 and the chassis 80 are assembled (see, e.g., FIGS. 6-7), a housing having an interior space is formed. The chassis 80 has a side wall 82 that defines a number of compartments including a motor recess 83 and battery compartments 84. Each of the battery compartments 84 are configured for housing a single battery, such as a AA battery, in the chassis 80. The battery contacts 76a, 76b are mounted at opposite ends of the each of the battery compartments 84.

Tuning now to FIG. 8, A fan housing 40 includes a side wall 41 having regularly spaced openings 42 that define outlets for permitting air mixed with air treatment chemical to exit the interior space of the wearable chemical dispenser 18. In the non-limiting example embodiment shown in FIG. 8, the openings 42 define a semicircular area and extend around the entirety of side wall 41 of the fan housing 40.

Preferably, a flow path from the fan 60 to the openings 42 is unobstructed. Some other devices included a slide cover designed to shut off air flow by blocking the inlet vents and the exhaust vents. The intent was to minimize loss of actives while the unit is not in use by blocking off airflow across the dosed pad. The walls blocking the exhaust vents and the geometries supporting them occupied large space and caused the device to increase in size. These blocking walls are eliminated in the dispenser 18 without increased loss in actives ingredient. These example opening configurations contribute to a balance of airflow and minimal power consumption for the wearable chemical dispenser 18.

Looking at FIGS. 8 and 16, a motor 93 is positioned in the space 83 in the chassis 80. The motor 93 is in electrical communication with the tactile switch 75 for powering the motor when the cam 32 on slide cover 30 contacts the on/off switch actuator, which in turn contacts tactile switch 75 to turn on the motor 93. The motor 93 includes a drive shaft 95 that is connected to the tubular mounting element 66 on the rotor 61. As a result, the motor 93 can rotate the fan 60. A battery door 96 (see FIG. 8) covers the battery housing 84 in the chassis 80. The battery door 96 includes mounting tabs 97. A bottom cover 102 is fastened to the chassis 80 by way of one or more fasteners. In FIG. 8, six screws 72 are used to fasten together, in order, PCB 70, chassis 80 and bottom cover 102.

Figure 3:
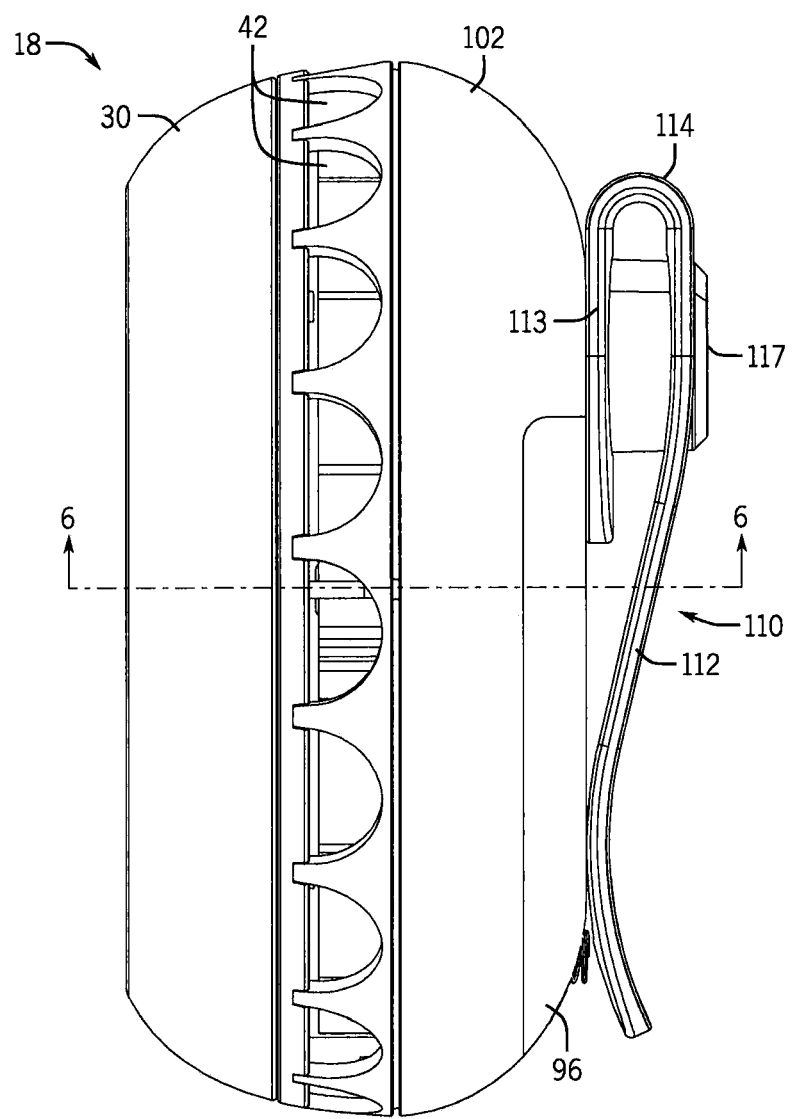
FIG. 3 is a right side elevation view of the dispenser of FIG. 1.
Figure 4:
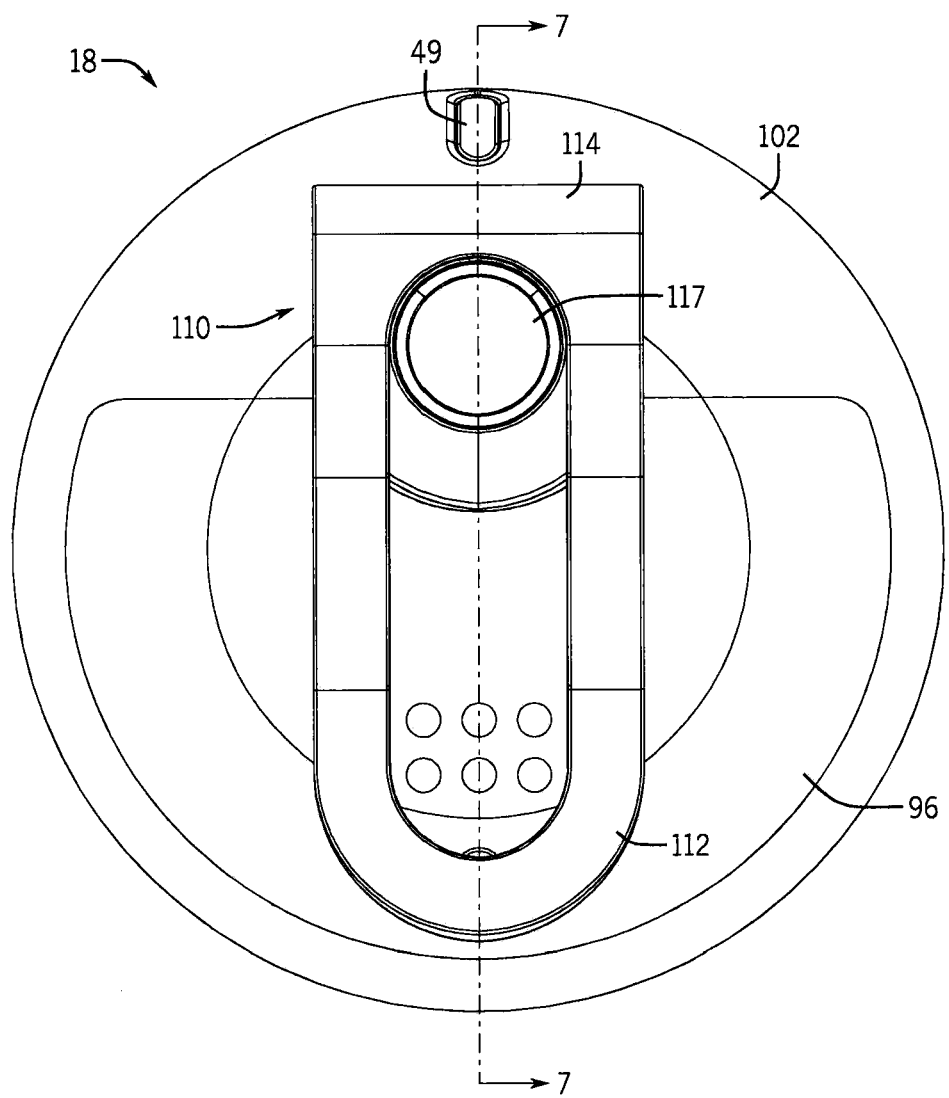
FIG. 4 is a rear elevation view of the dispenser of FIG. 1.
Figure 5:
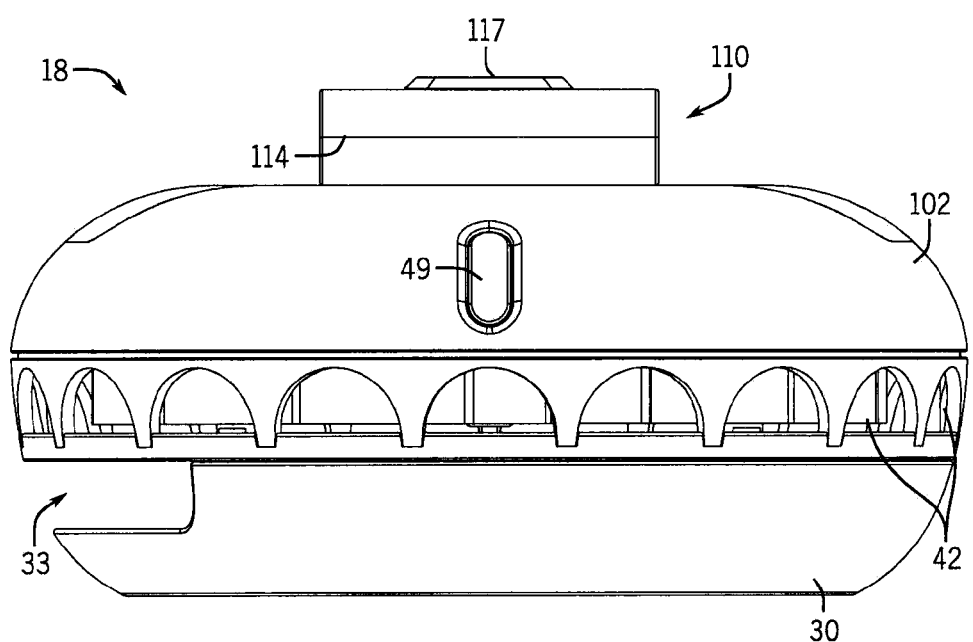
FIG. 5 is a top plan view of the dispenser of FIG. 1.
Figure 6:
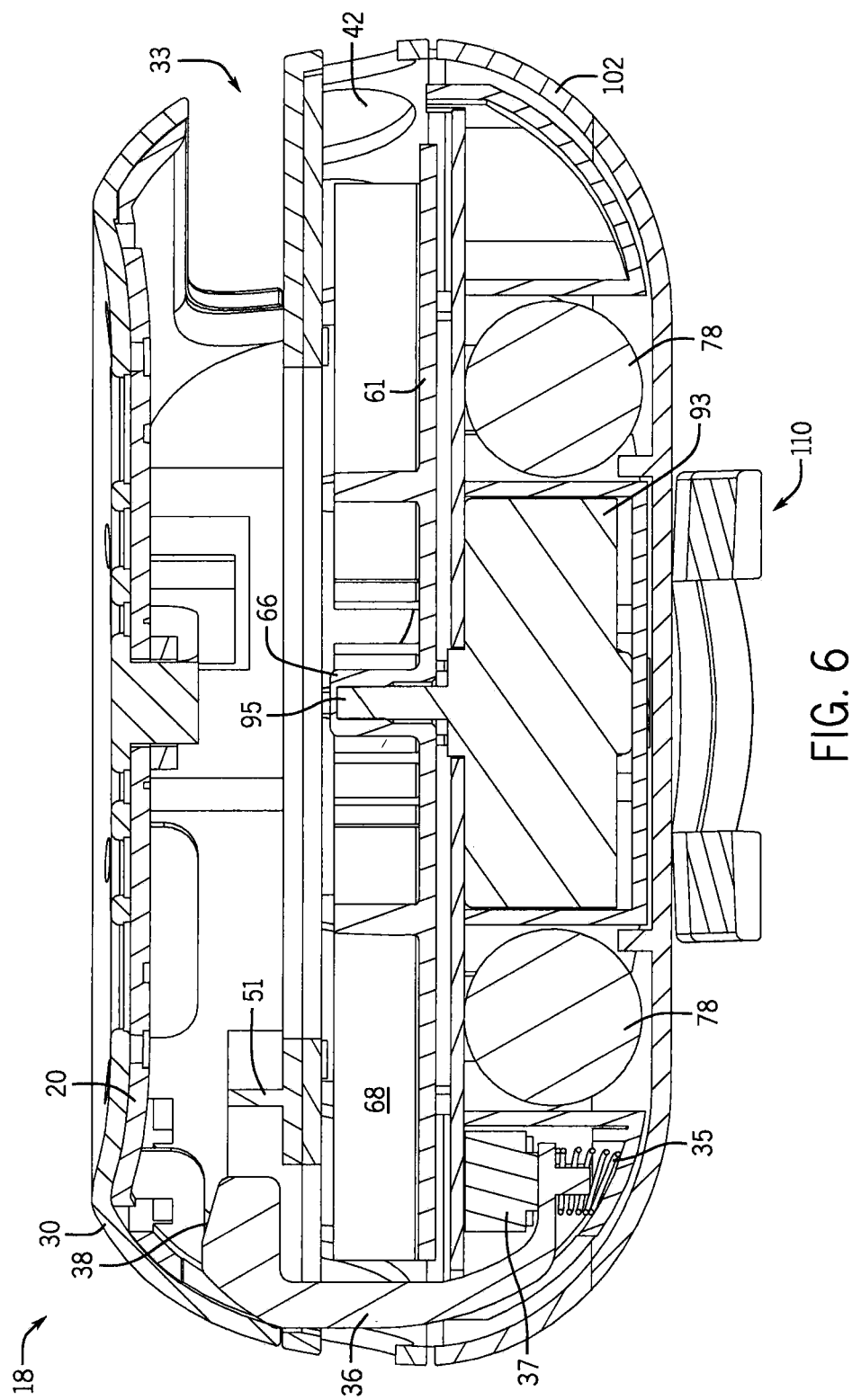
FIG. 6 is a cross-section view taken along line 6-6 of FIG. 4.
Figure 7:
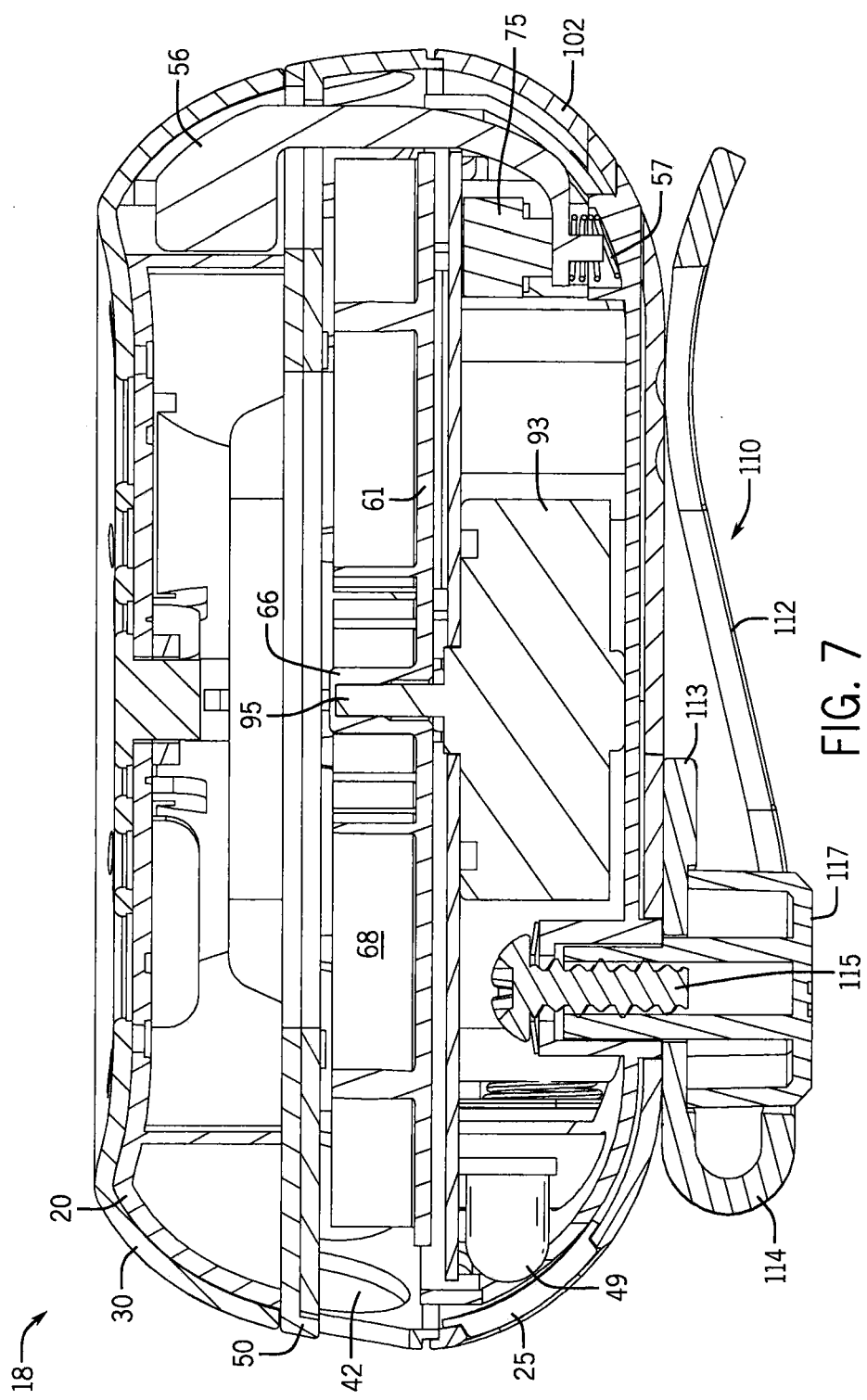
FIG. 7 is a cross-section view taken along line 7-7 of FIG. 4.

Looking now at FIGS. 3-4 and 8, means for clipping the wearable chemical dispenser 18 to a user's clothing (e.g., a belt or a pocket) are shown. The wearable chemical dispenser 18 includes a clip 110 having a front section 112 that is spaced at its upper end from a rear section 113 by a top section 114 that connects the front section 112 and the rear section 113. At the lower end of the clip 110, the front section 112 and the bottom cover 102 may be in contact until flexed apart by a user. A through hole 103 extends through the chassis 80, the bottom cover 102 and clip 110. The through hole 103 is can be aligned with a clip pivot cover 117. The pivot cover 117 includes two concentric cylindrical elements with the inner cylinder configured to couple to a fastener. In FIG. 8 the fastener is a screw 115. The screw 115 is inserted through the through hole 103 of the chassis 80, though bottom cover 102 and clip 110, and into pivot cover 117 opposing the front section 112 of the clip 110 such that the clip 110 can rotate.

Regarding component construction, the top housing section 20, slide cover 30, support structure 45 of the refill unit 44, fan housing 40, frame 50, fan 60, chassis 80, battery door 96, bottom cover 102, and clip 110 may be formed from a suitable polymeric material such as polyethylene, polypropylene, or polyester.

In operation, the wearable chemical dispenser 18 will be clipped on a belt, purse or the like using clip 110 for that purpose. When a user rotates the top housing section 20 from the 'lock' position into the 'on' position, the openings 31 of the slide cover 30 align with the apertures 24 that are radially arranged in the top wall 23 of the top housing section 20. The cam projection 32 of the slide cover 28 is driven into the on/off switch actuator 56 which then contacts the tactile switch 75 to signal to the power supply to power the fan 60 by way of motor 93. Air is drawn by the fan 60 of the wearable chemical dispenser 18 in through apertures 24 and the openings 31. As the air passes through fabric substrate 48, the air treatment chemical mixes into the air and a mixture of air and air treatment chemical is then blown radially out openings 42 (preferably down along pants or dresses). A user can rotate the clip 110 as described above to change the path of the mixture of air and air treatment chemical.

While the present device is primarily intended to be used as a wearable item carried with a human when outdoors, it can also be laid flat, with the clip 110 downward and the slide cover 30 upward, on a picnic table or the like. When used in this manner it can provide protection to an area during a picnic or similar outdoor activity.

Another non-limiting example of a wearable chemical dispenser 218 is shown in FIGS. 17-30. In one version of this embodiment, the dispenser 218 is a portable, fan-based device for dispensing a chemical, such as an insect repellent, from a replaceable cartridge 244 (hereinafter, the 'refill unit') that is housed in the dispenser 218. Furthermore, the dispenser 218 can be attached with a clip 310 to a user's clothing (e.g., a belt) and is operated by rotating a slide cover 230 on the front face of the dispenser. The slide cover 230 can rotate between three settings including: (i) a 'load' setting for inserting/positioning the refill unit 244 in the dispenser 218, (ii) a 'lock' setting for securing the refill unit 244 in the dispenser 218, and (iii) an 'on' setting for operating the fan 260 to actively dispense the chemical in the refill unit 244.

One feature of the dispenser 218 is an indicator of useful life 249. In one example, the useful life indicator 249 is an LED that is lit to indicate to a user when the refill unit 244 should be replaced (e.g., the amount of chemical repellent remaining in the refill unit 244 may no longer effective for repelling insects). The useful life of the refill unit 244 is determined with an on/off switch actuator 237 (see FIGS. 26-28), which is triggered upon rotation of the slide cover 230 into the 'on' position.

FIGS. 17-21 show views of the assembled wearable chemical dispenser 218. The wearable chemical dispenser 218 includes a slide cover 230 disposed on a top housing section 220 (see FIG. 23). Slide cover 230 and top housing 220 have side walls 229, 222 characterized by a generally spherical segment that extends from top walls 228, 223, respectively. In use, top wall 228 of slide cover 230 is typically frontally disposed and acts as a front cover in combination with top housing 220. A plurality of spaced apart apertures 224 are radially arranged in the top wall 223 of the top housing section 220. The apertures 224 provide an inlet for permitting air to enter into an interior space of the wearable chemical dispenser 218.

Slide cover 230 also possesses a plurality of spaced apart vent openings 231 radially arranged in top wall 228. The openings 231 provide an inlet for permitting air to enter into an interior space of the wearable chemical dispenser 218 when at least partially aligned with apertures 224 in top wall 223 of top housing 220. Slide cover 230 is coupled to the top housing section 220 such that the slide cover 230 can rotate with respect to the top housing section 220. Slide cover 230 can be rotated between three distinct positions including a 'load' position, a 'lock' position and an 'on' position. In the 'lock' position, the slide cover 230 shields the apertures 224 that are radially arranged in the top wall 223 of the top housing section 220. In the 'on' position, the openings 231 of the slide cover 230 at least partially align with the apertures 224 that are radially arranged in the top wall 223 of the top housing section 220.

Figure 24:
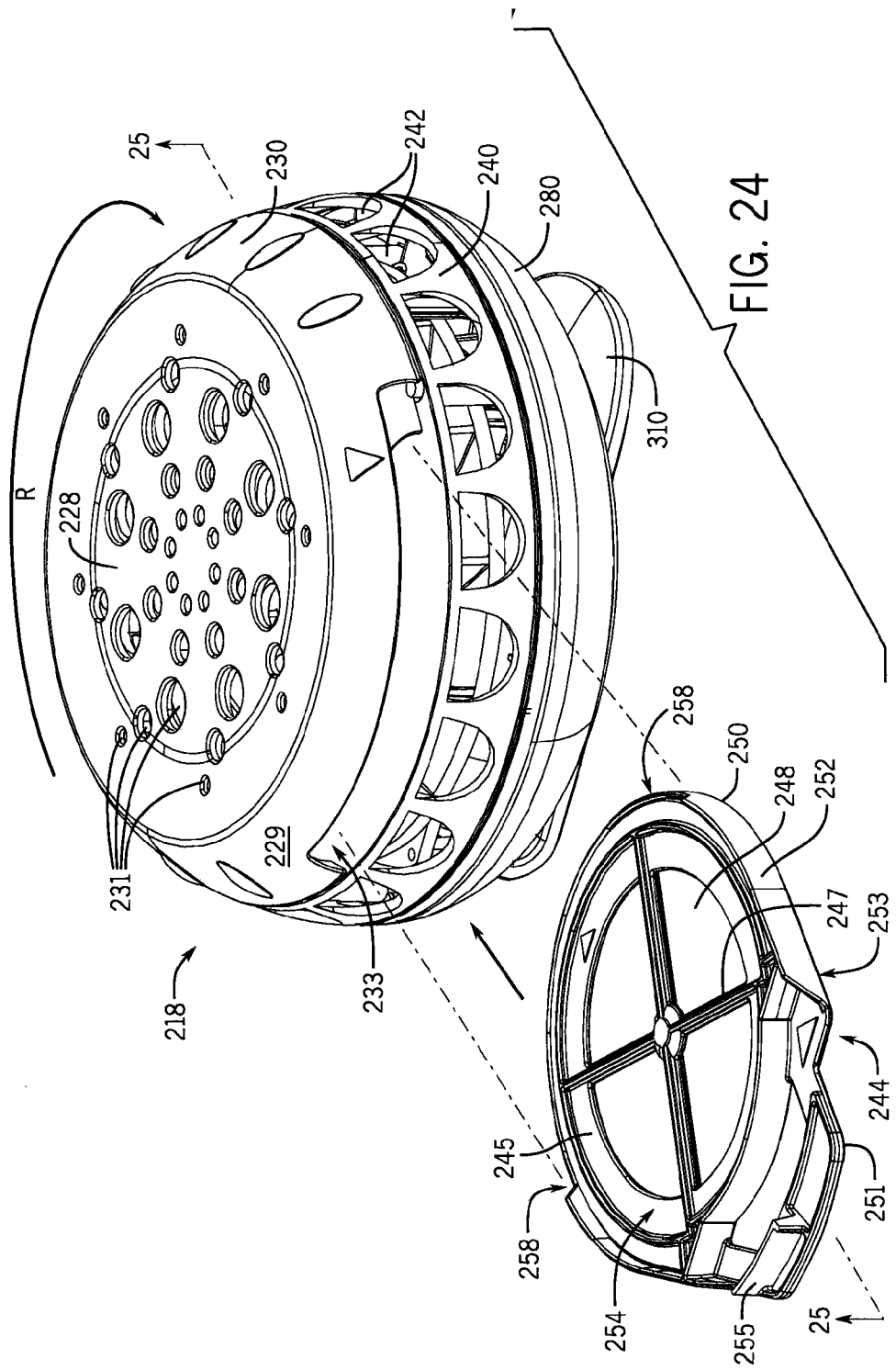
FIG. 24 is a left, front perspective view of the dispenser of FIG. 17 illustrating a method of loading a refill unit into the dispenser.
Figure 25:
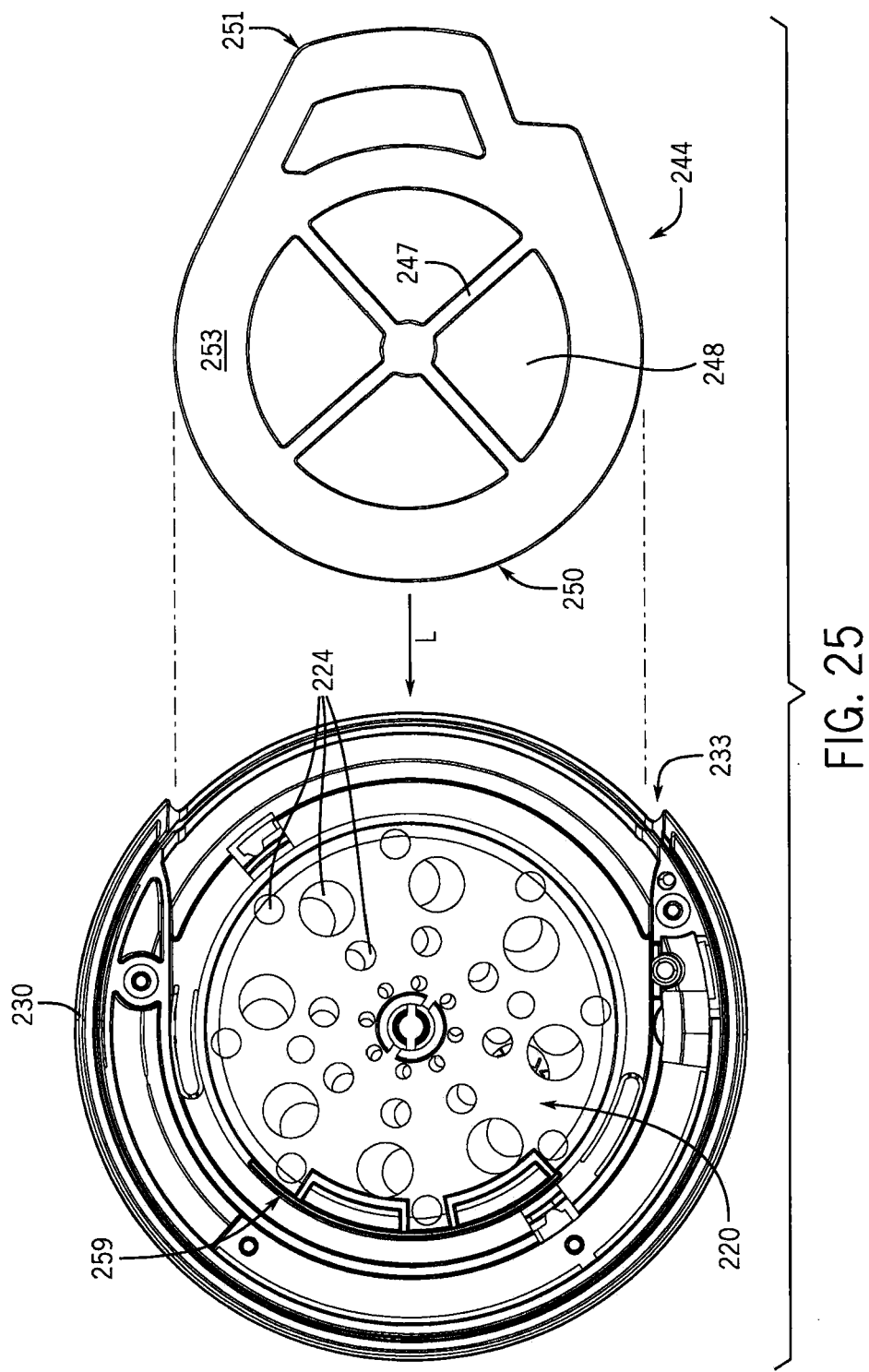
FIG. 25 is a view, partially in cross-section, taken along line 25-25 of FIG. 24 illustrating a method of loading a refill unit into the dispenser.
Figure 26:
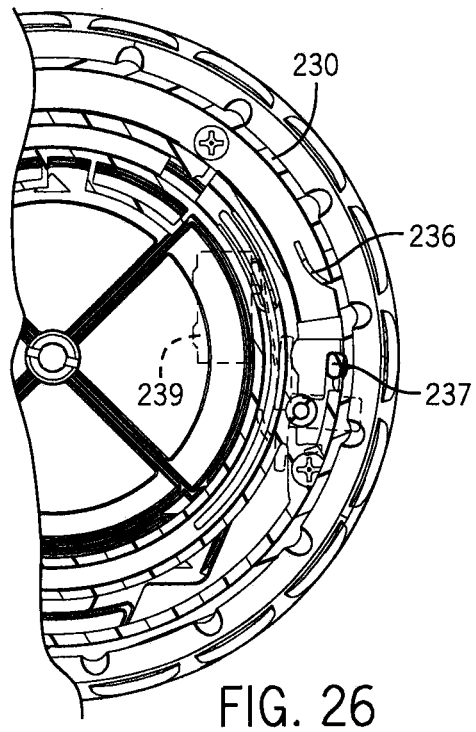
FIG. 26 is a partial cross-section view taken along line 26-26 of FIG. 18 illustrating the dispenser of FIG. 17 just prior to actuation of the on/off switch actuator.
Figure 27:
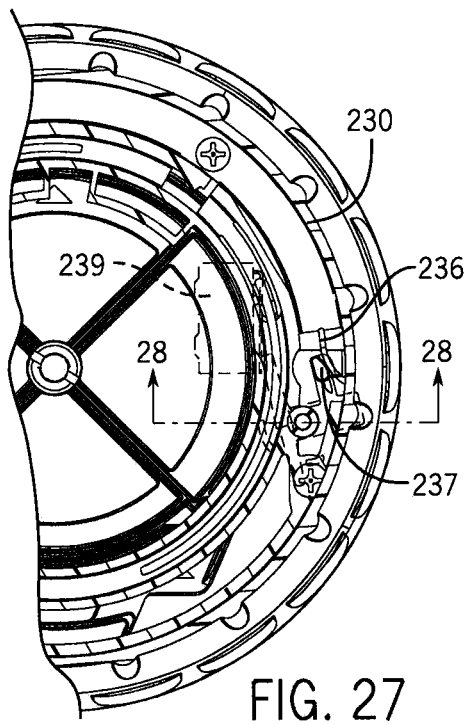
FIG. 27 is a partial cross-section view taken along line 26-26 of FIG. 18 illustrating the dispenser of FIG. 17 just after actuation of the on/off switch actuator.
Figure 28:
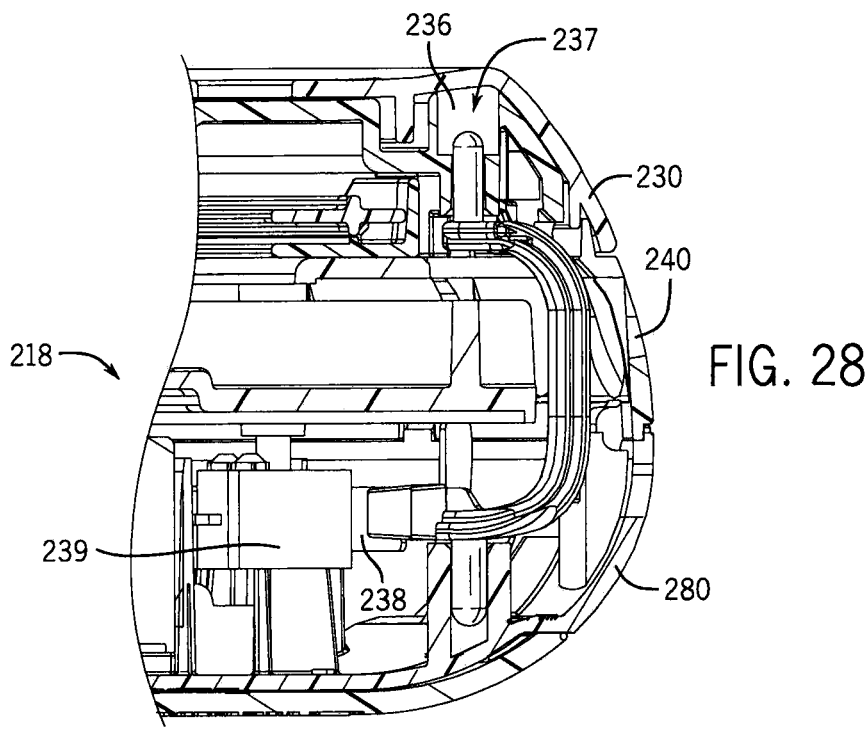
FIG. 28 is a detailed cross-section view taken along line 28-28 of FIG. 27 illustrating the dispenser of FIG. 17 after actuation of the on/off switch actuator during rotation of the of slide cover to the 'on' position.

As illustrated in FIGS. 24 and 25, a refill unit 244 is provided with the wearable chemical dispenser 218. In the 'loading' position, the slide cover 230 and top housing 220 align to form a refill loading slot 233 through which the refill unit 244 can pass in order to be loaded into the interior space in wearable dispenser 218. When slide cover 230 is rotated in direction R to either the 'lock' position or the 'on' position, a portion of side wall 229 of slide cover 230 is positioned over (and therefore prevents access to) loading slot 233.

As shown in FIGS. 24 and 25, the refill unit 244 has a generally slab-like support structure 245. In top plan view, the refill unit 244 has an essentially pear shaped overall appearance, with a generally circular portion at a first end 250 and a tabular portion at a second end 251. There is a spoke support 247 across a circular opening through the refill unit 244. Across the spoke support 247 is positioned a fabric substrate 248. When air is drawn in, the air passes through the fabric substrate 248. The choice of the fabric, and its porosity, the speed of the air flow, and the vapor pressure of the active ingredient, are the main factors in coordinating the speed of use up of the active with counter for activating a useful life indicator 249. A non-limiting example refill unit has a twelve hour active use life (i.e., fan on). Indicator 249 is designed to provide an alert to a user of the wearable dispenser 218 upon the expiration of the useful life of the refill unit. Methods for determining when to activate indicator 249 are described in detail below. The fabric substrate 248 can have the same properties (e.g., active release rates, active ingredients, impregnation material, pressure drop, fabric materials and basis weights, evaporation properties, etc.) as the fabric substrate 48 described above.

Still referring to FIGS. 24 and 25, the refill unit 244 has an outer wall 252 that extends from a first surface 253 of the refill unit 244. The outer wall 252 has a notch 258 formed in a section of the outer wall 252 adjacent the first end 250 of the refill unit 244. The notch 258 is designed to pass under a stop rib 259 on the bottom side of the top housing section 220 (see FIG. 25) when a consumer properly loads (in direction L) the refill unit 244 into the refill loading slot 233 of the dispenser 218. If the user attempts to incorrectly load the refill unit 244 into the refill loading slot 233 with the first end 250 of the refill unit 244 facing into the interior space of the housing and the first side 253 of the refill unit 244 facing the top housing section 220, the first end 250 of the refill unit 244 will contact the stop rib 259 and prevent complete insertion of the refill unit 244 into the refill loading slot 233 of the dispenser 218. If the user attempts to incorrectly load the refill unit 244 into the refill loading slot 233 with the second end 251 of the refill unit 244 facing into the interior space of the housing and the second side 254 of the refill unit 244 facing the top housing section 220, a tab 255 (see FIG. 24) that extends away from the second end 251 of the refill unit 244 will contact the stop rib 259 and prevent complete insertion of the refill unit 244 into the refill loading slot 233 of the dispenser 218. If the user attempts to incorrectly load the refill unit 244 into the refill loading slot 233 with the second end 251 of the refill unit 244 facing into the interior space of the housing and the first side 253 of the refill unit 244 facing the top housing section 220, the second end 251 of the substrate will contact the stop rib 259 and prevent complete insertion of the refill unit 244 into the refill loading slot 233 of the dispenser 218.

Figure 22:
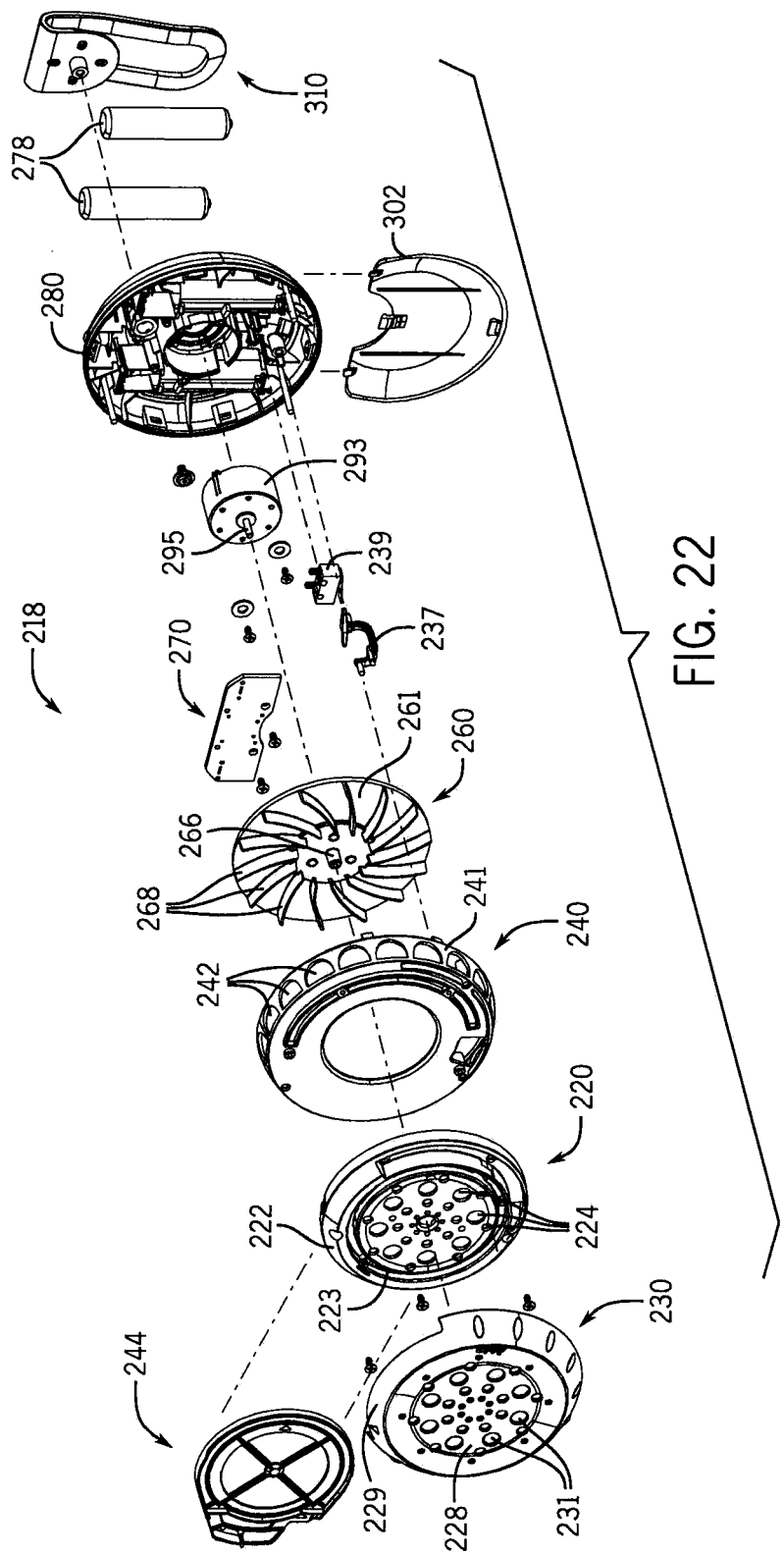
FIG. 22 is an exploded perspective view of the dispenser of FIG. 17.
Figure 23:
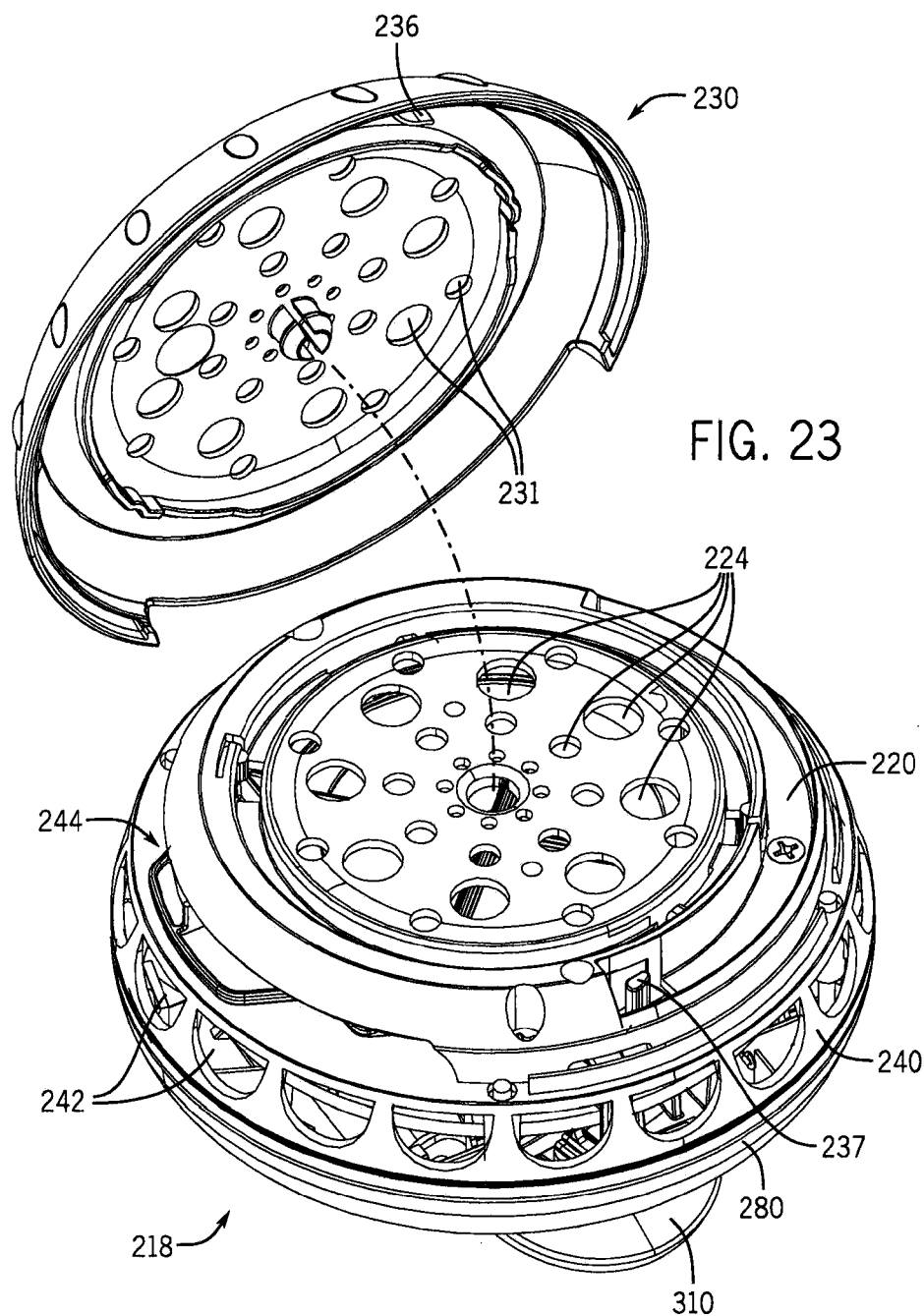
FIG. 23 is a left, bottom, front perspective view of the dispenser of FIG. 17 showing the alignment of the slide cover with the top housing.

Referring to FIG. 22, the dispenser 218 is assembled such that refill unit 244 is situated adjacent fan housing 240 and fan 260. This arrangement allows air to be drawn through refill unit 244. As described further on, this air, which is now mixed with chemical released from refill unit 244 can pass through openings 242 in sidewall 241 of fan housing 240.

Still looking at FIG. 22, there is shown a fan 260 of the wearable chemical dispenser 218. The centrifugal fan 260 has a generally disk shaped rotor 261 that includes a tubular mounting element 266 on the axis of the rotor 261. The preferred fan 260 includes fourteen fan blades 268. It has been discovered that a fan configuration, which results in an ideal balance of airflow and minimal power consumption for the wearable chemical dispenser 218, includes twelve to eighteen fan blades. Preferably, the fan produces an average volumetric flow rate of air of 1.4 to 3 cubic feet per minute (with the refill unit 244 installed) over the life (e.g., at least eight, and most preferably at least twelve hours) of a refill unit 244. Typically, the fan will operate at 3000-5000 rpm. In one example wearable chemical dispenser 218, over the life (e.g., twelve hours) of a refill unit 244, the consumed power from the power supply is 0.20 watts or less. In one example embodiment, over a twelve hour life of a refill unit 244, the consumed power from the power supply is about 0.19 watts while maintaining an average volumetric flow rate of air of at least 1.6 cubic feet per minute over the twelve hour period. When using a battery for the power supply, the voltage will vary during discharge. However, the power consumed can be determined from the total energy consumed divided by the total time.

The wearable chemical dispenser 218 includes an electrical power supply. In the example embodiment shown, batteries 278 provide the electricity. Looking at FIGS. 26-28, the slide cover 230 includes a projection 236. When a user rotates the slide cover 230 from the 'lock' position of FIG. 26 to the 'on' position of FIG. 27, the projection 236 of the slide cover 230 is driven into the on/off switch actuator 237 which then contacts tab 238 (see FIG. 28) of a microswitch 239 to turn on the power supply. The on/off switch actuator 237 is biased away from the tab 238 when in the off position. The power supply is in electrical communication with printed circuit board (PCB) 270 acting as a controller. When a user activates the microswitch 239 to completes an electrical circuit with batteries 278 to supply power to PCB 70, a counter and the fan motor 293 are activated.

One method to accurately indicate to a user the end of the useful life of the refill unit 244 makes use of the counter. For example, the counter is triggered when the fan 260 is turned on (i.e., by rotating the slide cover 230 to the 'on' position). After a first predetermined amount of usage time (e.g., approximately 10 hours) as measured by the counter, the PCB 70 lights the LED useful life indicator 249 to alert the user it is time to replace both the refill unit 244 and the batteries 278. After a second predetermined amount of usage time (e.g., approximately 12 hours) based on a drop in battery voltage, the PCB 70 causes the dispenser 218 to turn off so the user has to replace the refill unit 244 and batteries 278 if they have not already done so. The first and second time periods may be varied depending on the construction of the refill unit 244 and the batteries 278.

Looking at FIG. 22, the wearable chemical dispenser 218 includes a chassis 280 for mounting various components of the wearable chemical dispenser 218 and for contributing to the control of air flow from the dispenser 218. The chassis 280 has a side wall 282 that defines a number of compartments including a motor recess and battery compartments. A fan housing 240 includes a side wall 241 having regularly spaced openings 242 that define outlets for permitting air mixed with air treatment chemical to exit the interior space of the wearable chemical dispenser 218. In the non-limiting example embodiment shown in FIG. 22, the openings 242 have a semicircular shape and are equally spaced substantially 360 degrees around the side wall 241 of the fan housing 240. The 360 degree side openings 242 provide more uniform dispersion and have energy advantages.

Still referring to FIG. 22, the motor 293 is positioned in a space in the chassis 280. The motor 293 is in electrical communication with the microswitch 239 for powering the motor when the projection 236 on slide cover 230 contacts the on/off switch actuator 237. The motor 293 includes a drive shaft 295 that is connected to the tubular mounting element 266 on the rotor 261. As a result, the motor 293 can rotate the fan 260. Preferably, the motor has a current draw such that power of the device is 50 milliwatts or greater when the batteries 278 are fully charged. A bottom cover 302 is fastened to the chassis 280 by way of one or more fasteners.

Figure 18:
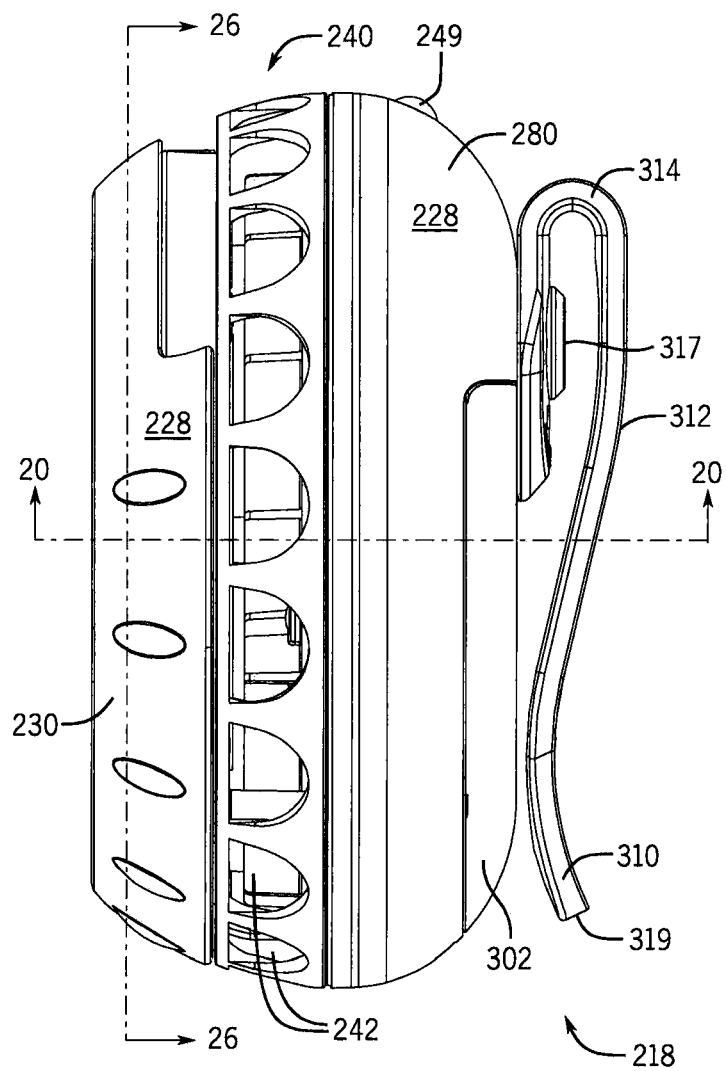
FIG. 18 is a right side elevation view of the dispenser of FIG. 17.
Figure 19:
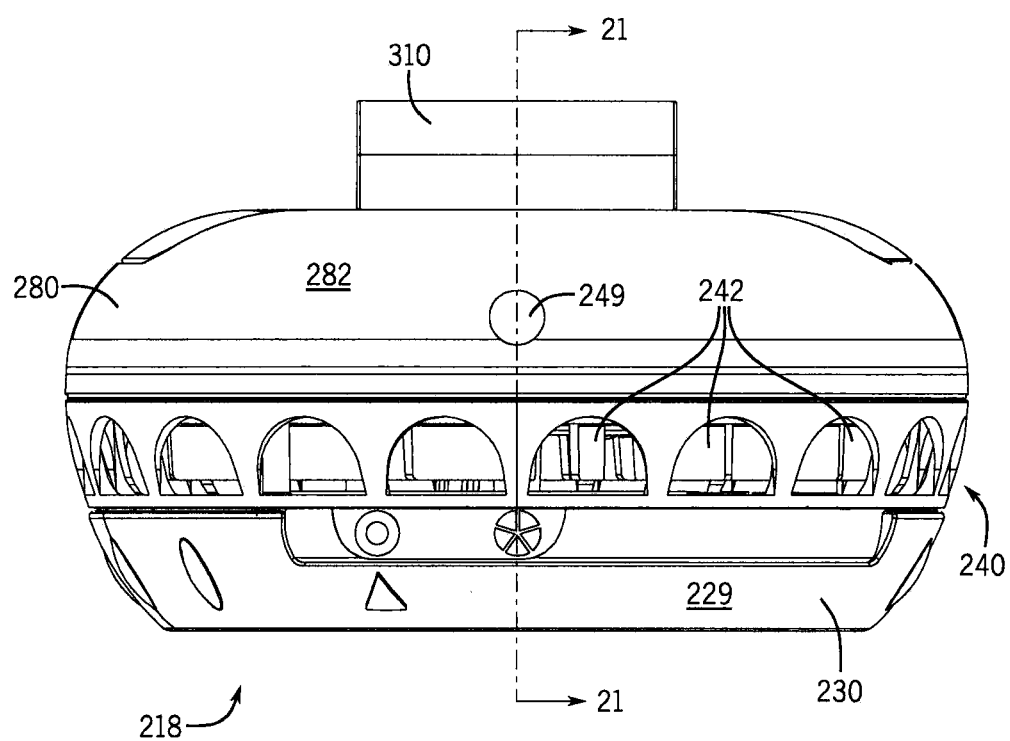
FIG. 19 is a top plan view of the dispenser of FIG. 17.
Figure 20:
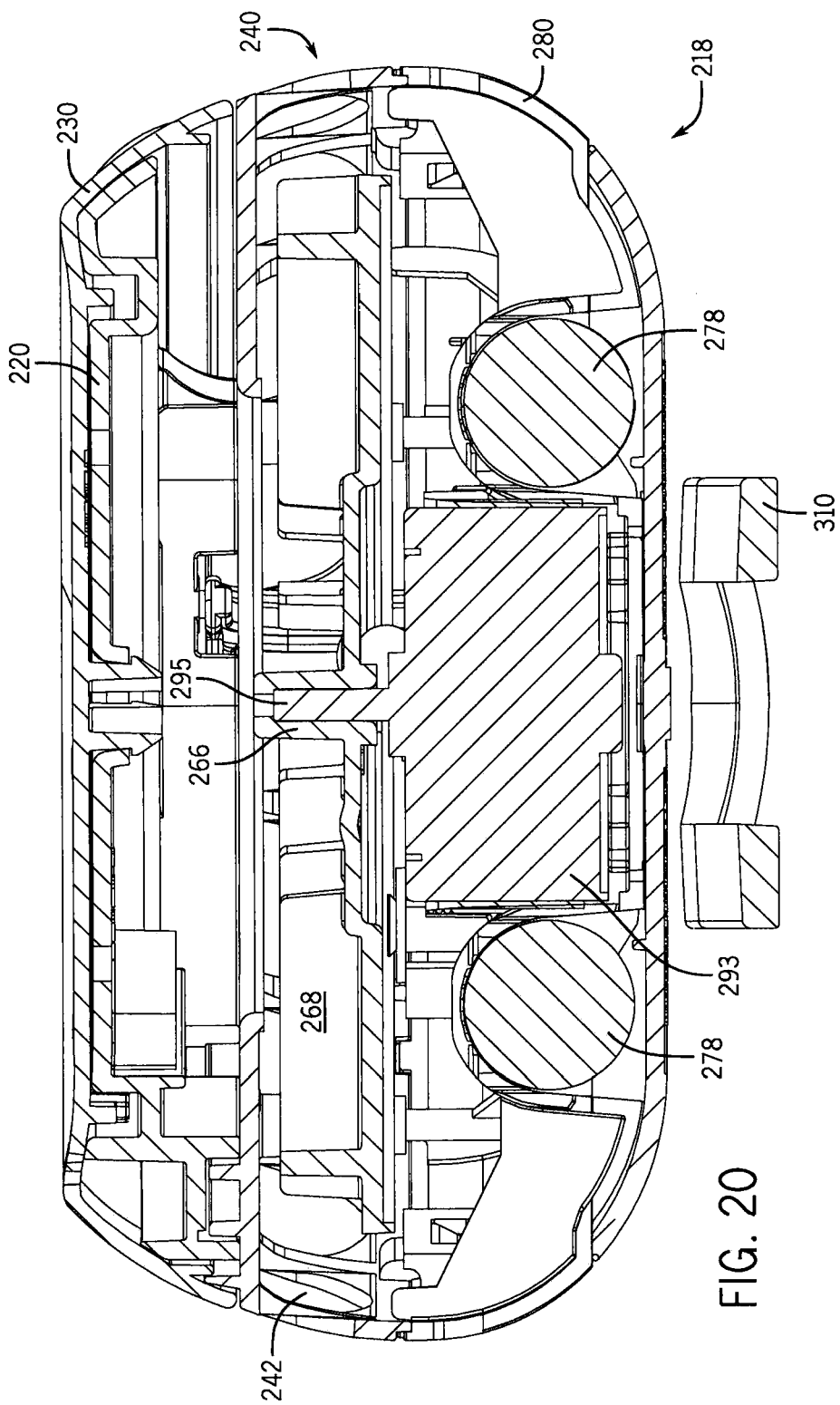
FIG. 20 is a cross-section view taken along line 20-20 of FIG. 18.
Figure 21:
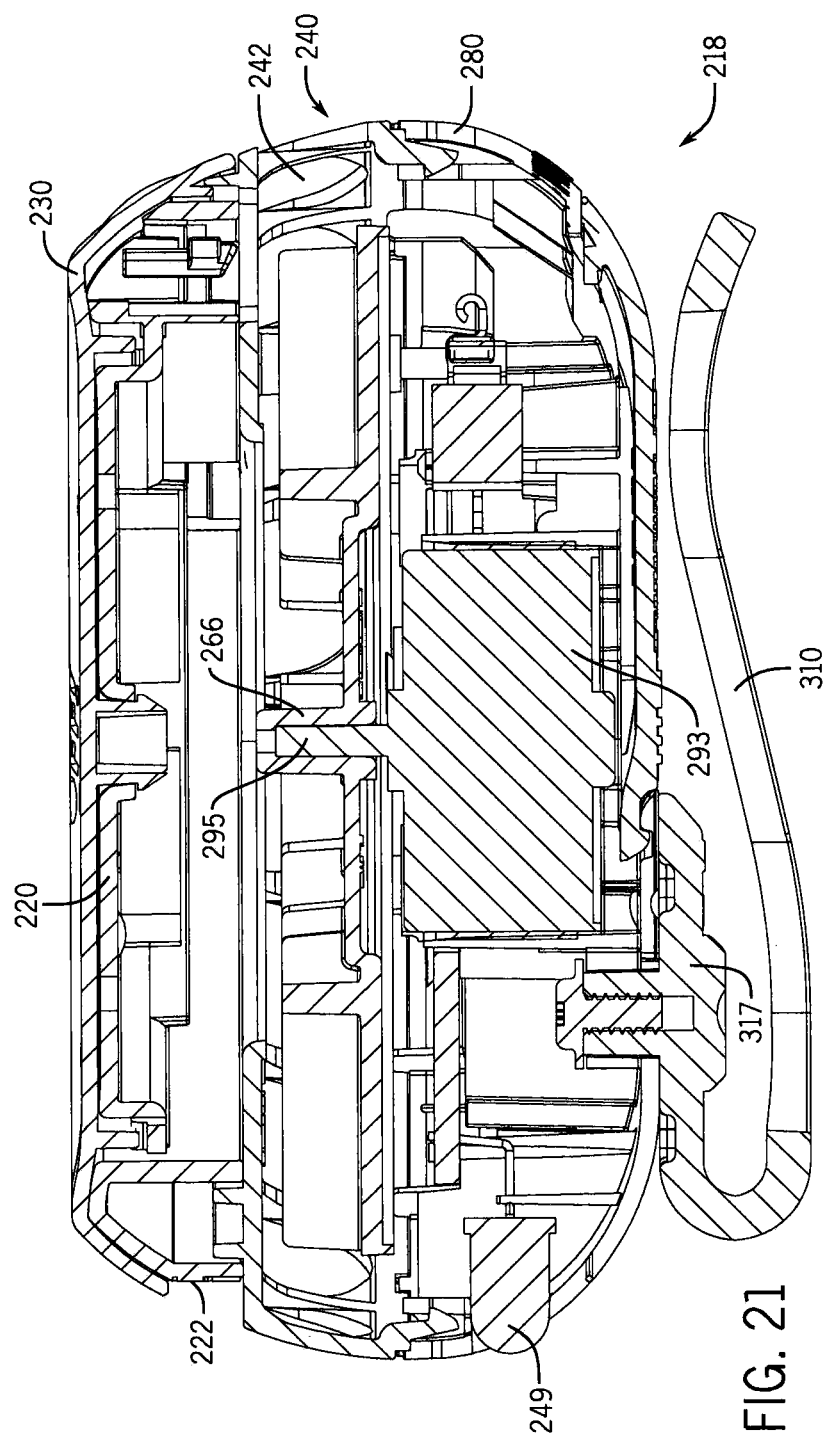
FIG. 21 is a cross-section view taken along line 21-21 of FIG. 19.
Figure 29:
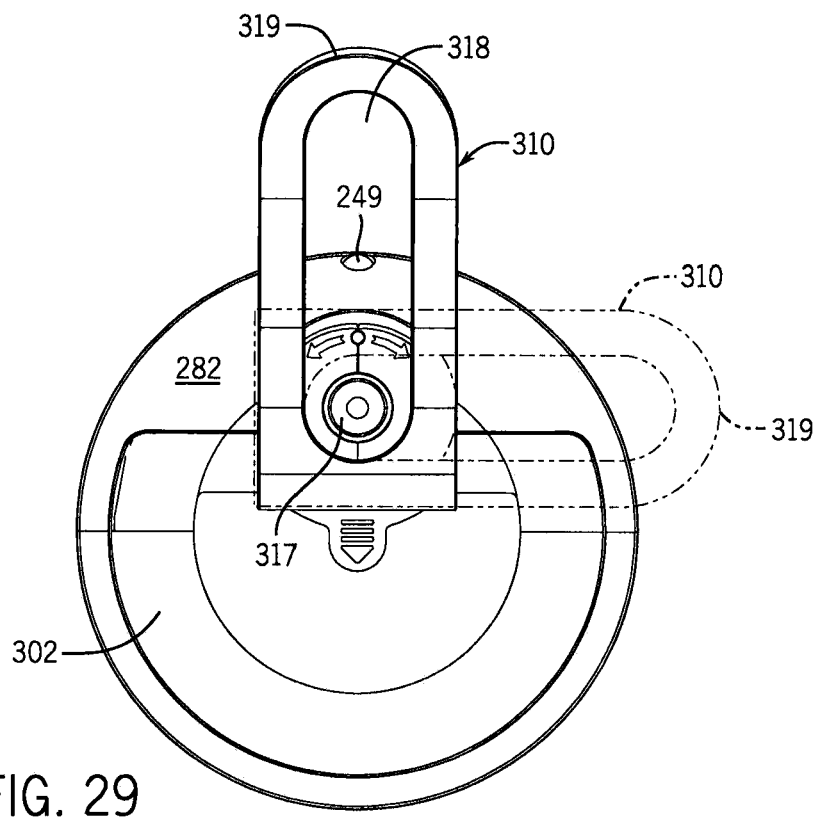
FIG. 29 is a rear elevation view illustrating the clip of the dispenser of FIG. 17 in alternative positions.
Figure 30:
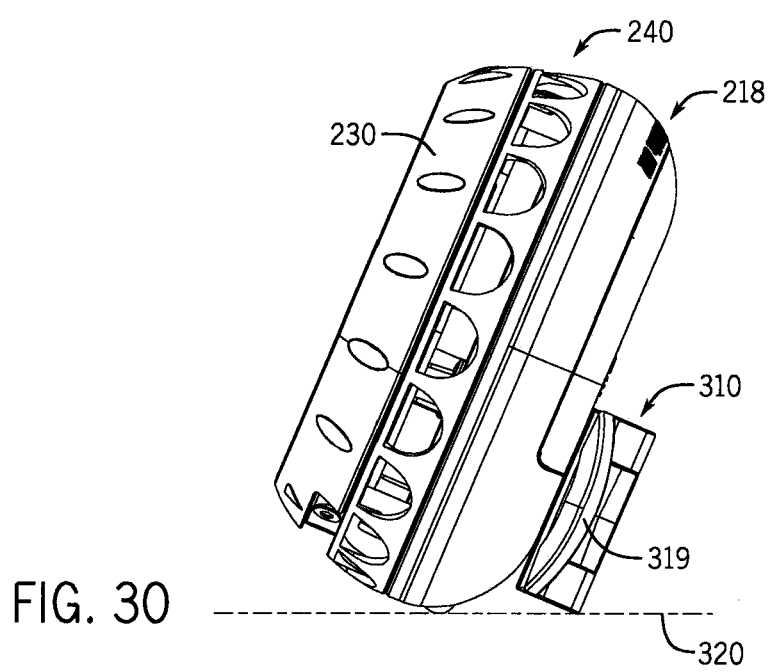
FIG. 30 is a side elevation view illustrating the dispenser of FIG. 17 positioned on a surface.

Looking now at FIGS. 18-22 and 29-30, the wearable chemical dispenser 218 includes a clip 310 having a front section 312 that is spaced at its upper end from a rear section 313 by a top section 314 that connects the front section 312 and the rear section 313. At the lower end of the clip 310, the front section 312 and the bottom cover 302 may be in contact until flexed apart by a user. A fastener 317 connects the clip 310 to the chassis 280 such that the clip 310 can rotate. The clip 310 can pivot 360 degrees and includes a slot 318. Referring to FIGS. 18 and 29, three useful positions of the rotatable clip 310 are shown. In FIG. 18, the curved end 319 of the clip 310 faces downward in relation to the useful life indicator 249. This is a first clip position typically used when the dispenser 218 is clipped on a user's clothing (e.g., belt). FIG. 29 shows a second clip position in which the curved end 319 of the clip 310 faces upward in relation to the useful life indicator 249. The second clip position is typically used when the dispenser 218 is hung from a hook or the like. FIG. 29 shows in dashed lines a third clip position in which the curved end 319 of the clip 310 faces laterally in relation to the useful life indicator 249. As shown in FIG. 30, the third clip position is typically used when the dispenser 218 is placed on a surface 320 (e.g., a table).

Regarding component construction, the top housing section 220, slide cover 230, support structure 245 of the refill unit 244, fan housing 240, fan 260, chassis 280, bottom cover 302, and clip 310 may be formed from a suitable polymeric material such as polyethylene, polypropylene, or polyester.

In operation, when a user rotates the top housing section 220 from the 'lock' position into the 'on' position, the vent openings 231 of the slide cover 230 at least partially align with the apertures 224 that are radially arranged in the top wall 223 of the top housing section 220. The projection 232 of the slide cover 228 is driven into the on/off switch actuator 237 which then contacts the microswitch 239 to signal to the power supply to power the fan 260 by way of motor 293. Air is drawn by the fan 260 of the wearable chemical dispenser 218 in through apertures 224 and the openings 231. As the air passes through fabric substrate 228, the air treatment chemical mixes into the air and a mixture of air and air treatment chemical is then blown radially out openings 242 (preferably down along pants or dresses). A user can rotate the clip 310 as described above to change the path of the mixture of air and air treatment chemical, or hand the dispenser 218, or place the dispenser 218 on a surface.

Various orientations of the vent openings 231 of the slide cover 230 and the apertures 224 of the top housing section 220 can be beneficial. The size and location of the vent openings 231 and the apertures 224 can be arranged to get efficacy with the apertures 224 not totally open. Under certain circumstances, a more closed design (e.g., with only ~30% of the area of the apertures 224 open) can give sufficient efficacy and air flow in cfm. Other devices typically have air vents as open as possible. In one non-limiting configuration, the vent openings 231 are ~33% open (projected area on the refill unit 244. It can be advantageous to have 25% to 50% open on each quadrant of the refill unit 244. The sizes of the vent openings 231 and the apertures 224 may vary within each quadrant with the largest holes located approximately half the distance between the center of the slide cover 230 and the outer periphery of the slide cover 230, and the smallest holes located toward the center of the slide cover 230.

Hence, the device is much more compact and lightweight, yet still effective. Further, the cost of operation from a battery standpoint is reduced. The device can more comfortably be used when seated, and provides greater control over dispensing direction. Also, installing a replacement active unit refill is easier. These advantages are achieved at lowered cost, and provide a reliable construction.

In the wearable dispenser, the intake grill size is designed to work in concert with an improved fan which falls within a specific range of fan blades, size and blade angle. A low current draw motor is recessed into the axial hub of the fan design. The airflow exits through 360 degrees of output vents. This combination of design features results in an ideal balance of airflow and minimal power consumption that results in a highly efficient system, which produces good insect repellency and usage duration in a relatively small, lightweight unit.

While example embodiments have been described above, it should be appreciated that there are numerous other embodiments of the invention within the spirit and scope of this disclosure. For example, the device can be powered by a different source of energy (e.g. a solar power panel or a weight responsive to motion of a wearer), other forms of actives can be dispensed along with or in substitution for the insect control ingredients (e.g. a fragrance or deodorizing chemical), and even when an insect control ingredient is dispensed it need not be one focused on controlling mosquitoes (e.g., chemicals for repelling other flying or crawling insects or pests can be used). Hence, the invention is not to be limited to just the specific embodiments shown or described.

INDUSTRIAL APPLICABILITY

Provided herein are wearable dispensing devices capable of dispensing insect control chemicals and/or other air treatment chemicals adjacent a human body.

All documents cited in the Detailed Description of the Invention are, in relevant part, incorporated herein by reference; the citation of any document is not to be construed as an admission that it is prior art with respect to the present invention.

What is claimed is:

1. A wearable device for dispensing an air treatment chemical, the device comprising:
   a circular housing comprising an inlet for permitting air to enter into an interior space of the housing, and a plurality of outlets spaced substantially 360 degrees around the housing, the outlets permitting air mixed with air treatment chemical to exit the interior space;
   a substrate dimensioned to be positioned in the housing via a slot in the housing, the substrate bearing an air treatment chemical;
   a centrifugal fan mounted within the housing, the fan being capable of moving air from the inlet adjacent the substrate so as to mix air treatment chemical into the moving air, and then deliver a mixture of air and air treatment chemical through the outlets to outside of the housing.

2. The device of claim 1 wherein:
   the inlet comprises a first section including a plurality of spaced apart apertures and a cover section including a plurality of spaced apart vent openings, and
   the cover section is movable from a first position in which the cover section covers the plurality of spaced apart apertures of the first section to a second position in which the plurality of spaced apart vent openings of the cover section are at least partially aligned with the plurality of spaced apart apertures of the first section.

3. The device of claim 2 further comprising:
   a power supply mounted within the housing; and
   a motor mounted within the housing, the motor being powered by the power supply and the fan being connected to the motor
   wherein the power supply includes a battery, and
   the motor has a current draw such that power of the device is 50 milliwatts or greater when the battery is fully charged.

4. The device of claim 2 wherein:
   the vent openings of the cover section include at least a first size of openings of a first inside diameter and a second size of openings of a second inside diameter smaller than the first inside diameter, and
   at least a first group of the first size of openings is arranged further away from a center of the cover section than a second group of the second size of openings.

5. The device of claim 2 wherein:
   the vent openings of the cover section include a plurality of sizes of openings, and
   a size of openings having the largest inside diameter is arranged about half way between a center of the cover section and an outer periphery of the cover section.

6. The device of claim 1 further comprising:
   a clip rotatably connected to an outer wall of the housing, the clip being structured to rotate 360 degrees with respect to the housing.

7. The device of claim 6, wherein:
   the clip includes a slot.

8. A refill adapted for use in a wearable device for dispensing an air treatment chemical wherein the device includes a housing comprising an inlet for permitting air to enter into an interior space of the housing, and an outlet permitting air mixed with air treatment chemical to exit the interior space, the refill comprising:
   a substrate dimensioned to be positioned in the housing via a slot in the housing, the substrate having a first end, a second end opposite the first end, a first side, and a second side opposite the first side, the substrate bearing an air treatment chemical,
   wherein the second side of the substrate includes an alignment profile that cooperates with an alignment structure in the slot such that the first end of the substrate faces away from an opening of the slot and the second side of the substrate faces the inlet when the substrate is positioned for use in the housing, and the alignment profile is partially defined by a tab that extends away from the second side of the substrate adjacent the second end of the substrate.

9. The refill of claim 8 wherein:
   the substrate includes an outer wall, and
   the alignment profile is partially defined by a notch in a section of the outer wall adjacent the first end of the substrate.

10. The refill of claim 9 wherein:
    the alignment structure in the slot comprises a stop rib extending away from the inlet.

11. The refill of claim 10 wherein:
    the notch travels past the stop rib when the substrate is inserted in the opening of the slot with the first end of the substrate facing into the interior space of the housing and the second side of the substrate facing the inlet.

12. A wearable device for dispensing an air treatment chemical, the device comprising:
    a housing comprising an inlet for permitting air to enter into an interior space of the housing, and an outlet for permitting air mixed with air treatment chemical to exit the interior space;
    a substrate positioned within the housing, the substrate bearing an air treatment chemical;
    a power supply mounted within the housing;
    a motor mounted within the housing, the motor being powered by the power supply;
    a fan mounted within the housing and connected to the motor, the fan being capable of moving air from the inlet adjacent the substrate so as to mix air treatment chemical into the moving air, and then deliver a mixture of air and air treatment chemical through the outlet to outside of the housing; and
    a switch for activating and deactivating the motor,
    wherein a top section of the housing is rotatably coupled to a bottom section of the housing, the top section of the housing being rotated to contact the switch and activate the motor.

13. The device of claim 12 wherein:
    the top section of the housing has a first position for positioning the substrate within the housing, and
    the top section of the housing has a second position for securing the substrate within the housing, and the top section of the housing has a third position for contacting the switch.

14. The device of claim 12 further comprising:
a controller in electrical communication with the switch and an indicator of useful life for the substrate, the controller executing a stored program to activate the indicator based on a signal from the switch.

15. The device of claim 14 wherein:
the controller executes the stored program to:
   (i) adjust a value of a counting device when the switch is contacted, and
   (ii) activate the indicator when the value of the counting device equals a predetermined value.

16. The device of claim 12, further comprising:
an actuator positioned within the housing, wherein the substrate actuates the actuator when the substrate is positioned within the housing; and
a controller in electrical communication with the switch, the actuator, and an indicator of useful life for the substrate.

17. The device of claim 16 wherein:
the controller executes a stored program to:
   (i) start adjusting a value of a counting device when the substrate actuates the actuator;
   (ii) adjust the value of the counting device when the motor is activated; and
   (iii) activate the indicator when the value of the counting device equals a predetermined value.

18. The device of claim 17 wherein:
the counting device includes a first timer and a second timer, and
actuation of the actuator initiates the first timer, and
activation of the motor initiates the second timer.

19. The device of claim 18 wherein:
the value of the counting device is adjusted based on first timing signals from the first timer and second timing signals from the second timer.

* * * * *